(12) United States Patent
Momose et al.

(10) Patent No.: US 8,367,424 B2
(45) Date of Patent: Feb. 5, 2013

(54) MICROCHIP AND METHOD OF USING THE SAME

(75) Inventors: Shun Momose, Kyoto (JP); Akinori Yokogawa, Kyoto (JP); Toshihiro Mori, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 160 days.

(21) Appl. No.: 12/250,592

(22) Filed: Oct. 14, 2008

(65) Prior Publication Data

US 2009/0098658 A1 Apr. 16, 2009

(30) Foreign Application Priority Data

| Oct. 15, 2007 | (JP) | 2007-267833 |
| Oct. 31, 2007 | (JP) | 2007-284212 |
| Oct. 31, 2007 | (JP) | 2007-284213 |
| Jan. 17, 2008 | (JP) | 2008-008154 |

(51) Int. Cl.
*G01N 21/41* (2006.01)
*G01N 21/01* (2006.01)

(52) U.S. Cl. .......... 436/164; 422/82.09; 422/82.08; 422/82.07

(58) Field of Classification Search ........ 422/82.09, 422/82.08, 82.07, 101, 136, 155, 500, 517; 436/164; 73/1.31, 1.73, 427, 426
See application file for complete search history.

(56) References Cited

U.S. PATENT DOCUMENTS

| 3,798,459 | A | * | 3/1974 | Anderson et al. ............ 250/576 |
| 3,889,296 | A | * | 6/1975 | Martin ................................. 2/9 |
| 3,899,296 | A | * | 8/1975 | Mailen et al. .................. 422/50 |
| 4,189,385 | A | | 2/1980 | Greenspan |
| 4,883,763 | A | | 11/1989 | Holen et al. |
| 5,590,052 | A | | 12/1996 | Kopf-Sill et al. |
| 5,764,356 | A | | 6/1998 | Iwase et al. |
| 6,696,022 | B1 | | 2/2004 | Chan et al. |
| 2002/0025583 | A1 | * | 2/2002 | Ellsworth et al. ............ 436/514 |
| 2002/0150503 | A1 | | 10/2002 | Tanaka et al. |
| 2004/0166551 | A1 | | 8/2004 | Moulds et al. |
| 2006/0160210 | A1 | | 7/2006 | Mori et al. |
| 2007/0125434 | A1 | | 6/2007 | Nakao |

(Continued)

FOREIGN PATENT DOCUMENTS

| JP | 60-238760 | 11/1985 |
| JP | 62-247248 | 10/1987 |

(Continued)

OTHER PUBLICATIONS

U.S. Appl. No. 12/467,404, filed May 18, 2009.

(Continued)

*Primary Examiner* — Krishnan S Menon
*Assistant Examiner* — Dwan A Gerido
(74) *Attorney, Agent, or Firm* — Fish & Richardson P.C.

(57) ABSTRACT

A microchip includes fluid circuits therein, formed by uniting together at least a first substrate that is a transparent substrate and a second substrate having grooves provided at the substrate surface and/or through holes penetrating in a thickness direction. The fluid circuits include a liquid reagent receptacle unit to store a liquid reagent, a quantification unit to quantify the liquid reagent or specimen, and an overflow liquid storage unit connected to the quantification unit to store the liquid reagent or specimen overflowing from the quantification unit during quantification. There is also provided a method of using the microchip.

8 Claims, 18 Drawing Sheets

U.S. PATENT DOCUMENTS

| | | |
|---|---|---|
| 2007/0212259 A1* | 9/2007 | Fujimura et al. ............ 422/61 |
| 2008/0156079 A1 | 7/2008 | Momose et al. |
| 2008/0296734 A1 | 12/2008 | Momose |
| 2009/0084738 A1 | 4/2009 | Momose |
| 2009/0104077 A1 | 4/2009 | Momose et al. |
| 2009/0111675 A1 | 4/2009 | Yokogawa et al. |
| 2009/0135407 A1 | 5/2009 | Kageyama et al. |
| 2009/0142232 A1 | 6/2009 | Okada et al. |
| 2009/0155125 A1 | 6/2009 | Michiue et al. |
| 2009/0232708 A1 | 9/2009 | Yokogawa et al. |

FOREIGN PATENT DOCUMENTS

| | | |
|---|---|---|
| JP | 8-334505 | 12/1996 |
| JP | 09-196739 | 7/1997 |
| JP | 2002-239317 | 8/2002 |
| JP | 2003-507026 | 2/2003 |
| JP | 2003-130883 | 5/2003 |
| JP | 2004-317489 | 11/2004 |
| JP | 2004-325172 | 11/2004 |
| JP | 2004-340702 | 12/2004 |
| JP | 2006-132990 | 5/2006 |
| JP | 2006-255584 | 9/2006 |
| JP | 2006-308447 | 11/2006 |
| JP | 2007-10435 | 1/2007 |
| JP | 2007-017342 | 1/2007 |
| JP | 2007-24851 | 2/2007 |
| JP | 2007-38484 | 2/2007 |
| JP | 2007-136379 | 6/2007 |
| JP | 2007-155441 | 6/2007 |
| JP | 2007-522441 | 8/2007 |
| JP | 2007-229631 | 9/2007 |
| WO | 02/23180 | 3/2002 |

OTHER PUBLICATIONS

U.S. Appl. No. 12/424,913, filed Apr. 16, 2009.
Notice of Grounds for Rejection for Japanese Patent Application No. 2007-284212, 7 pages (Feb. 21, 2012).
Notice of Grounds for Rejection for Japanese Patent Application No. 2007-267833, 4 pages (Mar. 13, 2012).
Japanese Patent Office, communication in Japanese Patent Application No. 2008-008154 (dated Jul. 31, 2012).

* cited by examiner

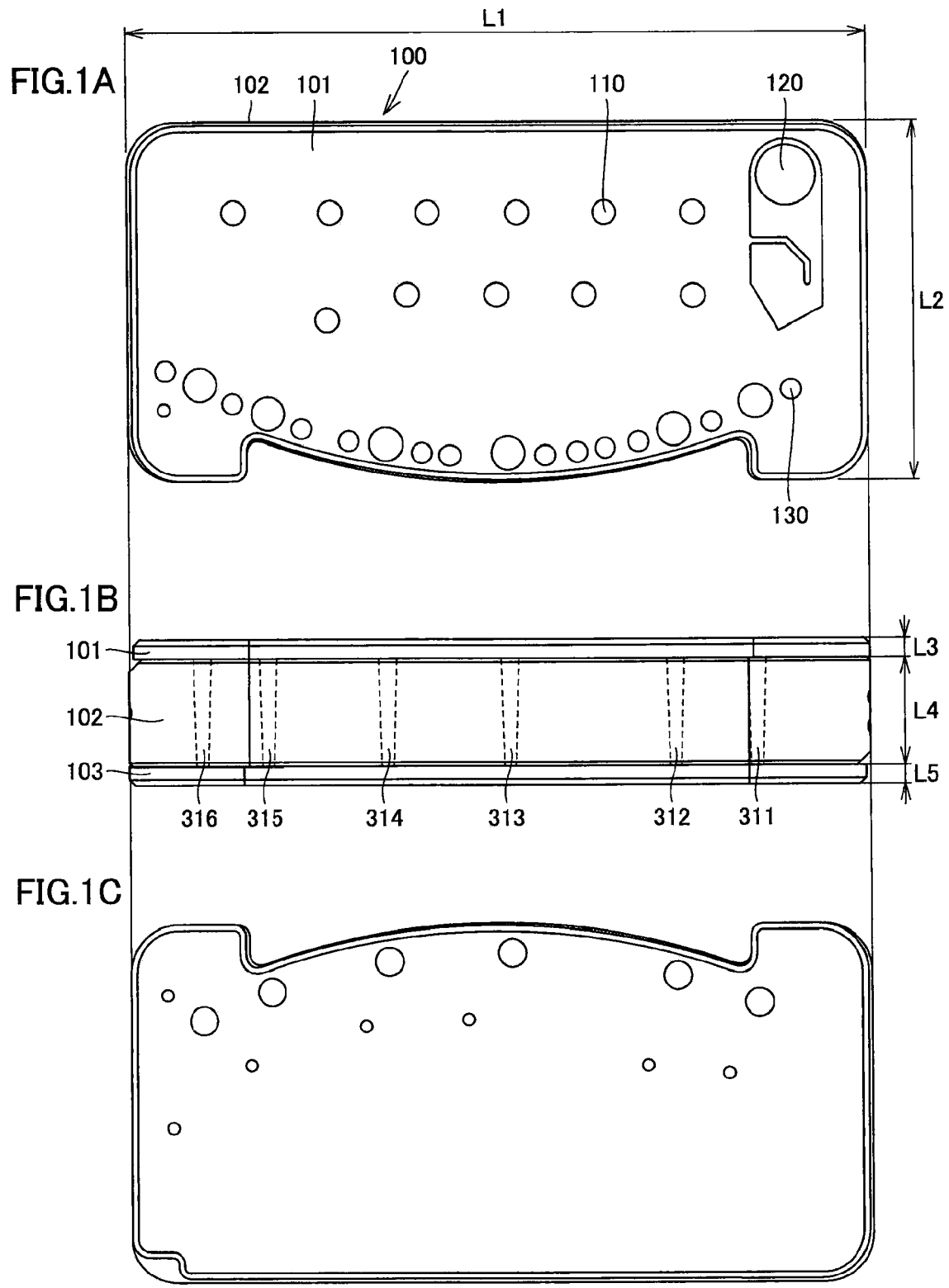

330 — 331b 311 331a

311

MICROCHIP AND METHOD OF USING THE SAME

BACKGROUND OF THE INVENTION

1. Field of the Invention

The present invention relates to a microchip valid for a μ-TAS(Micro Total Analysis System) and the like, suitable for use in environmental analysis, chemical synthesis and biochemical assays of DNA, protein, cells, immunity, blood and the like.

2. Description of the Background Art

In line with the recent increase in the importance of sensing, detecting and determining the quantity of chemical substances and biological material such as DNA (Deoxyribo Nucleic Acid), enzyme, antigen, antibody, protein, virus, and cells in the field of medical care, health, food product, development of medicine and the like, various biochips and microchemical chips (hereinafter, generically referred to as a microchip) that allow relevant measurement conveniently have been proposed (for example, Japanese Patent Laying-Open No. 2007-017342). A microchip is characterized in that the series of experiments and analytical operations carried out at laboratories can be performed within a chip that is several to 10 cm square and several millimeters to several centimeters in thickness. Accordingly, only a small amount of specimen and reagent is required, leading to reduction in cost. Assays can be performed with a high response rate and high throughput. Another advantage is that the examination result can be obtained immediately at the site where the specimen has been collected. A microchip can be used conveniently in biochemical examination such as a blood test.

A microchip has fluid circuits therein. The fluid circuits are mainly constituted of a plurality of sites such as a liquid reagent receptacle unit to store a liquid reagent directed to mixing or reacting with, or treating a specimen (for example, blood), a quantification unit to quantify a specimen and/or liquid reagent, a mixing unit to mix the specimen and liquid reagent, and a cuvette (detection unit) for optical measurement to examine and/or analyze the mixture, as well as minute channels appropriately connecting the sites. In use, a microchip is typically mounted on an apparatus (a centrifuge) that can apply centrifugal force to the chip. By applying centrifugal force to the microchip in an appropriate direction, measurement and mixture of a specimen and/or liquid reagent, in addition to introduction of the mixture to the optical measurement cuvette, can be effected. The examination and analysis of the mixture introduced into the optical measurement cuvette (for example, detection of a certain component in the mixture) can be implemented by directing light to the cuvette in which the mixture is stored and measure the transmissivity or the like.

In the examination and/or analysis based on the above-described microchip, a guarantee that the liquid treatment in the fluid circuits effected by application of centrifugal force is extremely critical. This is because, if such guarantee cannot be afforded, evaluation as to whether the result of the examination and analysis is reliable or not cannot be made. Unreliable situations include, for example, the case where the liquid reagent that should be stored in the liquid reagent receptacle unit at the time of using the microchip is not present at a predetermined location or is insufficient due to evaporation or drop off during transportation, the case where the introduced amount of specimen into the fluid circuits is insufficient, and the case where liquid leakage has occurred due to a defect in the fabrication of the microchip. In such cases, the quantified amount of liquid reagent and specimen will not be accurate, leading to incorrect resultant data from the examination and analysis. There is also the possibility of erroneous operation at the centrifuge equipment, which may impede appropriate fluid transfer. Therefore, a guarantee that the fluid in the fluid circuits is transferred to an appropriate site, fluid treatment is carried out appropriately, the amount of the specimen and/or liquid reagent is sufficient, without erroneous operation of the centrifuge equipment, is critical. However, the approach to actually introducing a specimen into the fluid circuits to conduct fluid treatment, and checking whether there is the aforementioned error, prior to the examination and analysis based on a microchip (actual usage), cannot be employed since a microchip is generally not reusable.

U.S. Pat. No. 5,590,052 discloses a method for confirming that the fluid introduced into a blood analysis system has flown to a predetermined site. This method includes the steps of directing light to a predetermined site, and detecting the passing light.

The microchip disclosed in the aforementioned Japanese Patent Laying-Open No. 2007-017342 is formed by uniting together a first substrate with grooves that correspond to fluid circuits, and a second substrate. The first and second substrates are united such that the surface of the first substrate where grooves are provided corresponds to the joining face. The microchip includes one layer of fluid circuits therein. As used herein, "one layer" implies that the microchip includes only one fluid circuit layer in the thickness direction of the microchip.

In a microchip directed to a blood test, various types of examinations are often performed using the blood plasma component in the whole blood. Therefore, fluid circuits in such a microchip generally includes a blood plasma separator unit to remove hematocytes from the whole blood introduced into the fluid circuits to extract and separate the plasma component.

SUMMARY OF THE INVENTION

In the conventional method of confirming that the fluid introduced into the blood analyzer has flown to a predetermined site, the blood analyzer must be filled with the fluid along the entire width at the predetermined site to identify the absence or presence of the fluid by measuring transmitting light. This means that the amount of fluid introduced into the blood analyzer must be increased if the blood analyzer is thick. Therefore, the benefit of allowing examination and/or analysis with a minute amount of fluid at the microchip, if the aforementioned conventional method is applied thereto, will be degraded.

Furthermore, when the transmitting light is to be measured to confirm that fluid has flown to a predetermined site in a microchip, a transparent substrate with respect to light must be employed for at least the light channel region of the detected light. This imposes the problem that the configuration of the microchip is rendered complex, and the degree of freedom in designing a microchip is degraded.

Moreover, when light is directed to a predetermined site in order to confirm arrival of the fluid at the predetermined site, there was a problem that, although the presence of the fluid at the predetermined site can be confirmed, the amount of the fluid at that predetermined site cannot be detected. In other words, the event of an insufficient amount of the specimen and/or liquid reagent caused by some error as described above cannot be detected.

In view of the foregoing, an object of the present invention is to provide a microchip improved in reliability, allowing detection of an insufficient amount of a specimen and/or liquid reagent as well as a fault such as an erroneous operation at a centrifuge, requiring only a minute amount of liquid, to guarantee, immediately before and during use of a microchip, that the fluid treatment in fluid circuits according to application of centrifugal force has been carried out appropriately, for every microchip, and a method of using the microchip.

The present invention is directed to a microchip including fluid circuits therein, formed by uniting together at least a first substrate that is a transparent substrate, and a second substrate having grooves provided at a substrate surface and/or through holes penetrating in a thickness direction. The fluid circuits include a liquid reagent receptacle unit storing a liquid reagent, at least one quantification unit to quantify the liquid reagent or a specimen, and at least one overflow liquid storage unit to store the liquid reagent or specimen overflowing from the quantification unit during quantification.

The microchip of the present invention may be a microchip including two layers of fluid circuits therein, formed by uniting together a first substrate that is a transparent substrate, a second substrate having grooves provided at both surfaces of the substrate and through holes penetrating in a thickness direction, and a third substrate. The overflow liquid storage unit is the site irradiated with light to detect the presence or absence of the liquid reagent or specimen overflowing from the quantification unit.

In the present invention, the microchip including two layers of fluid circuits therein may include a plurality of overflow liquid storage units. In this case, the fluid circuits at the side of the first substrate, of the two layers of fluid circuits, preferably includes all the overflow liquid storage units.

In the case where the microchip of the present invention includes a plurality of overflow liquid storage units, the plurality of overflow liquid storage units preferably are disposed on the circumference of the same circle at the surface of the second substrate.

The second substrate is preferably an opaque substrate, and more preferably a black substrate. In addition, the fluid circuits of the present invention may include at least one liquid reagent quantification unit to quantify the liquid reagent, and at least one specimen quantification unit to quantify the specimen. In this case, an overflow liquid storage unit is connected to at least one of the quantification units. Preferably, an overflow liquid storage unit is connected to each quantification unit. The fluid circuits may further include a mixing unit to mix the quantified specimen and the quantified liquid reagent, and a detection unit to examine and analyze the obtained mixture.

The present invention also provides a method of using the microchip set forth above, including the steps of introducing a liquid reagent or specimen into the quantification unit by applying centrifugal force, and detecting absence or presence of the liquid reagent or specimen in the overflow liquid storage unit by directing light from the first substrate side to the overflow liquid storage unit and measuring an intensity of light reflected therefrom. The detection of the absence or presence of the liquid reagent or specimen can be carried out by obtaining a ratio of the intensity of reflected light obtained by directing light to the overflow liquid storage unit from the first substrate side before the liquid reagent or specimen is introduced into a quantification unit to the intensity of reflected light obtained by directing light to the overflow liquid storage unit from the first substrate side after the liquid reagent or specimen is introduced into a quantification unit.

The method of using the microchip of the present invention may further include the step of detecting the absence or presence of a liquid reagent in the liquid reagent receptacle unit by directing light from the first substrate side to the liquid reagent receptacle unit to measure the intensity of light reflected therefrom. The detection of absence or presence of a liquid reagent can be carried out by obtaining the ratio of the intensity of reflected light obtained by directing light from the first substrate side to the liquid reagent receptacle unit, before the liquid reagent is introduced to the liquid reagent receptacle unit, to the intensity of reflected light obtained by directing light from the first substrate side to the liquid reagent receptacle unit, after the liquid reagent is introduced to the liquid reagent receptacle unit. The method of using the microchip of the present invention may further include the step of detecting absence or presence of a liquid reagent or specimen in at least one site selected from the liquid reagent quantification unit, the mixing unit, and the detection unit by directing light from the first substrate side to the at least one site and measuring the intensity of light reflected therefrom.

According to the present invention, detection can be made of an insufficient amount of a specimen and liquid reagent as well as a fault such as an erroneous operation at a centrifuge, requiring only a minute amount of liquid, during actual use of a microchip (during examination, analysis, and the like of a specimen) to guarantee that the fluid treatment in fluid circuits according to application of centrifugal force has been carried out appropriately. Therefore, a microchip improved in reliability can be provided by the present invention.

The aforementioned conventional "one layer type" microchip has the following problems (1) to (3). There is a need for a microchip that can overcome such problems.

(1) A one-layer type microchip must have the area of the substrate increased in order to form desired fluid circuits. Therefore, (i) the uniting area in affixing two substrates together is increased, leading to difficulty in obtaining flatness at the two substrates. Accordingly, welding failure will readily occur in welding the substrates together such as by laser welding, thermal welding, ultrasonic welding, and welding employing an adhesive. (ii) The uniting area in affixing two substrates together is increased, leading to difficulty in obtaining pressure evenness at the time of substrate welding. Accordingly, welding failure will readily occur in welding the substrates together. (iii) If the pressure at the time of welding is increased and/or a large amount of adhesive is employed in view of alleviating such welding failure, leakage of the resin constituting the substrate and/or run off of the adhesive may occur to block the minute pattern (grooves) formed at the surface of the substrate. (iv) In the case where leakage of the resin constituting the substrate and/or run off of the adhesive occurs, uniformity in the shape of the fluid circuits among microchips cannot be achieved. In addition, the volume of the quantification unit in the fluid circuits will vary, disallowing accurate measurement. In view of such problems, it was difficult to form intricate channel patterns and increase the scale of integration and density of fluid circuits in a one-layer type microchip.

(2) A one-layer type microchip will have a mixture of deep grooves and shallow grooves formed within one fluid circuit layer. (i) The width of the rib constituting the grooves is increased to maintain the aspect ratio of the mold directed to forming grooves in the substrate. Therefore, the likelihood of deviation in the dimension accuracy and variation in the dimension among mnicrochips, due to leakage of an adhesive or resin during welding, increases. (ii) When the substrate is fabricated by injection molding or imprinting, the region of shallow grooves will correspond to the bottom region of a mold. Therefore, fabrication of a mold accommodating the minute channel region is rendered difficult, resulting in poor mass production. (iii) In the case where there is a mixture of deep grooves and shallow grooves in one fluid circuit layer, the occupying ratio of the fluid circuits to the microchip cannot be increased. It is difficult to increase the scale of integration and density of fluid circuits.

The above problem (2) will be described in further detail with reference to the drawings. FIG. 23 is a schematic sectional view of a configuration of a mold to form a substrate with grooves constituting fluid circuits, employed for a conventional microchip. FIG. 24 is a schematic sectional view of a microchip formed using the substrate obtained from the mold of FIG. 23. For a substrate constituting a microchip, a plastic substrate, for example, can be employed. A substrate with grooves constituting fluid circuits can be produced by injection molding employing a mold with a transfer configuration. As shown in FIG. 23, the recess and projection in a mold 1701 (the transfer configuration of the grooves in a substrate) can be cut out using an end mill or the like. Consider the case where a substrate including both deep grooves and shallow grooves are to be formed. When a shape corresponding to shallow grooves is to be provided in the mold, a long end mill blade 1702 is required since cutting must be effected down to a deep region in the mold. End mill blade 1702 must have a diameter corresponding to the length. In other words, when a substrate including both deep grooves and shallow grooves is to be produced, a long and thick end mill blade must be employed to produce a companion mold.

As a result, a width W of a rib 1803 constituting shallow grooves at an upper substrate 1801 obtained from the mold of FIG. 23 is increased due to the diameter of the end mill blade. Accordingly, the area of contact between upper substrate 1801 and a lower substrate 1802 to be united is increased. Such increase in the area of contact will cause more leakage of the substrate material when the substrates are united together by, for example, fusing and welding the uniting faces. This induces deviation in the dimension accuracy of the fluid circuits and/or variation in the dimension among microchips.

Moreover, in the case where deep grooves and shallow grooves are formed in a mixed manner in one fluid circuit layer, there will be a space S that cannot be used for the fluid circuits, as shown in FIG. 24. Thus, it will be difficult to increase the scale of integration and density of fluid circuits (3) Application of centrifugal force towards a microchip can be implemented by mounting a microchip on a rotatable stage of a centrifuge, and spinning the stage. The rotating diameter of a stage must be increased since the area of the one-layer type microchip is large. This results in the increase of the size and power consumption of the centrifuge.

The present invention is directed to overcoming these problems, and an object according to another aspect is to provide a microchip with a sufficiently small substrate area (microchip area), increased in the scale of integration and density of fluid circuits.

According to the present invention, a microchip is provided, formed by uniting together a first substrate, a second substrate having grooves provided at both surfaces of the substrate and a plurality of through holes penetrating in a thickness direction, and a third substrate in the cited order. The microchip includes a first fluid circuit constituted of grooves provided at a surface of the first substrate facing the second substrate and at a surface of the second substrate facing the first substrate, and a second fluid circuit constituted of grooves provided at a surface of the third substrate facing the second substrate and at a surface of the second substrate facing the third substrate.

The first and second fluid circuits preferably communicate via at least one of the plurality of through holes.

Each of the first and second fluid circuits preferably includes at least one site selected from the group consisting of a liquid reagent receptacle unit to store a liquid reagent, a liquid reagent quantification unit to quantify the liquid reagent, a specimen quantification unit to quantify a specimen, and a mixing unit to mix the specimen and liquid reagent.

The grooves provided at the surface of the second substrate facing the first substrate is preferably deeper than the grooves provided at the surface of the second substrate facing the third substrate.

In the microchip of the present invention, preferably only the first fluid circuit includes one or a plurality of liquid reagent receptacle units, and preferably only the second fluid circuit includes one or a plurality of liquid reagent quantification units and one or a plurality of specimen quantification units.

The microchip of the present invention preferably further includes at least one detection unit, formed of a cavity constituted of at least one of the plurality of through holes, the surface of the first substrate facing the second substrate, and the surface of the third substrate facing the second substrate, and connected to the first or second fluid circuit.

The first substrate, the second substrate, and the third substrate are preferably formed of styrene-butadiene copolymer.

The first substrate and the third substrate are preferably transparent substrates. The second substrate is preferably a transparent substrate, more preferably a black substrate.

Since the microchip of the present invention includes fluid circuits of two layers, increase in the scale of integration and density of fluid circuits is allowed. Thus, fluid circuits that allows fluid treatment of a more complex level can be formed. Moreover, the substrate area (microchip area) can be reduced by employing fluid circuits of two layers. Thus, the flatness of each substrate at the time of uniting the substrates can be ensured, leading to the likelihood of obtaining pressure evenness over the entire substrate. Therefore, welding failure can be prevented or suppressed. Preventing or suppressing welding failure allows improvement in the mass production of microchips.

In the case where blood collected from a person with hyperlipidemia or with symptoms thereof is to be examined using a microchip directed to a blood test, the separated plasma component will include a component such as lipid that is insoluble with respect to the plasma component, impeding an accurate examination and analysis on the plasma component. Namely, if the mixture introduced into the detection unit includes an insoluble matter such as lipid, the directed light in optical measurement, when employed in the detection of the property component in the mixture, will be disturbed by the presence of such insoluble matter. There was a problem that accurate measurement data could not be obtained. Furthermore, the presence of such insoluble matter disallows accurate quantification of the plasma component, leading to the problem that proper measurement data cannot be obtained.

The present invention is directed to solving the problem set forth above. An object of the present invention is to provide a microchip for a blood test that can remove a component that may disturb the examination and analysis from a sample of whole blood, prior to mixture with a liquid reagent, allowing accurate examination and analysis.

In addition, the present invention provides a microchip for a blood test, including a blood plasma separation unit to separate a blood plasma component from a sample including whole blood introduced into the microchip. The blood plasma separation unit includes a suspension removal unit to remove suspensions present in proximity to the surface of the plasma blood component. The suspension removal unit includes one or a plurality of discrete columnar structures, and a suspension storage unit to store the removed suspensions. The columnar structure preferably has a triangular cross section.

The suspension removal unit may includes a plurality of discrete columnar structures, disposed in a plurality of rows. The suspension is, for example, lipid.

Since lipid and the like included in the whole blood sample can be removed in advance by the microchip of the present invention, a blood test can be carried out accurately without being disturbed by the lipid and the like.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 1A, 1B and 1C represent the outer shape of an example of a microchip according to the present invention.

DESCRIPTION OF THE PREFERRED EMBODIMENTS

Figure 2A:
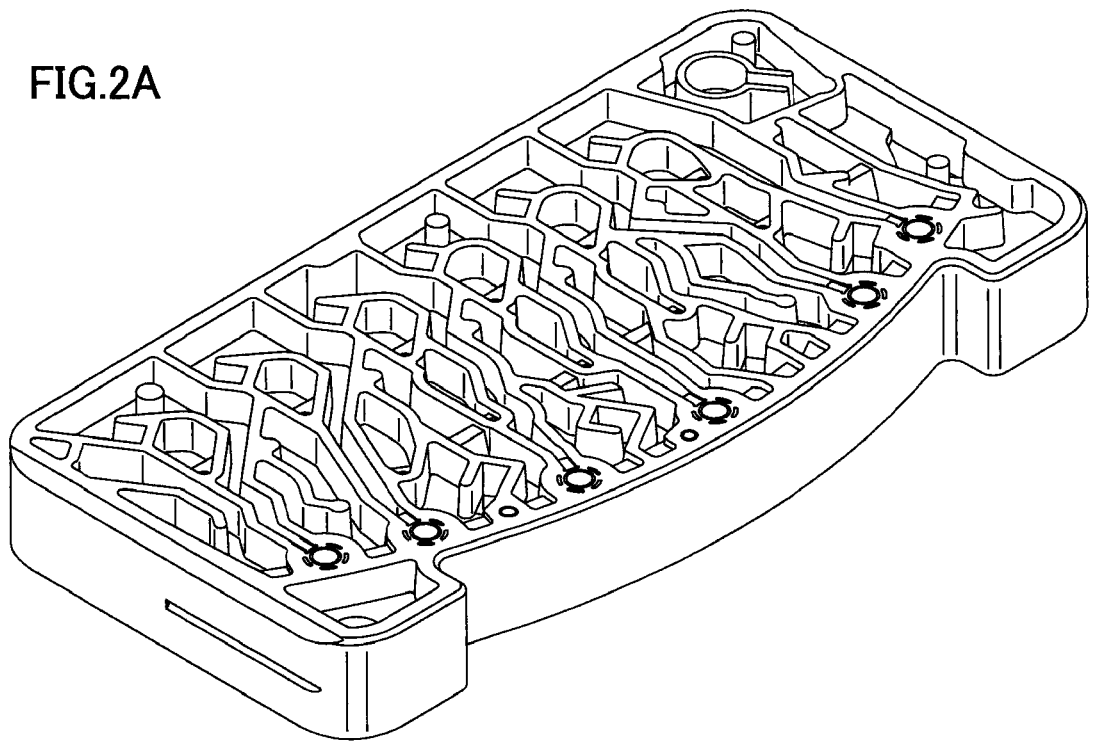
FIGS. 2A and 2B are perspective view of an example of fluid circuits formed at a second substrate of a microchip of the present invention.

Embodiments of the present invention will be described hereinafter with reference to the drawings. In the drawings, the same or corresponding elements have the same reference characters allotted, and description thereof will not be repeated. The scales in dimension such as the length, size, and width in the drawings are modified appropriately for the sake of simplification, and do not represent the actual scale dimension.

First Embodiment

The present invention will be described in detail based on FIGS. 1A, 1B and 1C that are a top view, side view, and bottom view, respectively, of an example of a microchip of the present invention. Referring to FIGS. 1A, 1B and 1C, a microchip 100 according to a first embodiment of the present invention is formed by uniting together a first substrate 101 that is a transparent substrate, a second substrate 102 that is a black substrate, and a third substrate 103 that is a transparent substrate, in the cited order (refer to FIG. 1B). The length of these substrates is, though not particularly limited to, approximately 62 mm in the lateral direction (L1 in FIG. 1) and approximately 30 mm in the vertical direction (L2 in FIG. 1) in the present embodiment. The thickness of first substrate 101 (L3 in FIG. 1), second substrate 102 (L4 in FIG. 1) and third substrate 103 (L5 in FIG. 1) is, though not particularly limited to, approximately 1.6 mm, approximately 9 mm, and approximately 1.6 mm, respectively.

First substrate 101 includes a liquid reagent inlet 110 (a total of 11 inlets in the present embodiment) penetrating in the thickness direction, and a specimen inlet 120 to introduce a specimen (for example, whole blood) into the microchip fluid circuits. As used herein, "specimen" refers to a sample (for example, whole blood) that is the subject of various chemical synthesis, examination, analysis, and the like, introduced into the fluid circuits, or a certain component separated from the sample in microchip 100 (for example, plasma component separated from the whole blood). A liquid reagent is already stored in a liquid reagent receptacle unit in the fluid circuits, prior to actual usage (examination, analysis, and the like of a specimen) of microchip 100, and is a substance used for mixture with or reaction with the specimen, or treatment of the specimen. Microchip 100 generally has a liquid reagent introduced through liquid reagent inlet 110, which is then sealed by a label or the like to be presented for actual use.

Second substrate 102 includes grooves formed at opposite surfaces, and a plurality of through holes penetrating in the thickness direction. By uniting first substrate 101 and third substrate 103 with second substrate 102, two layers of fluid circuits are formed in microchip 100. Hereinafter, the fluid circuits constituted of grooves provided at the surface of first substrate 101 facing second substrate 102 and at the surface of second substrate 102 facing first substrate 101 is referred to as "first fluid circuit". The fluid circuits constituted of grooves provided at the surface of third substrate 103 facing second substrate 102 and at the surface of second substrate 102 facing third substrate 103 is referred to as "second fluid circuit". The two layers of fluid circuits may communicate with each other via through holes penetrating in the thickness direction, formed in second substrate 102. Detection units 311, 312, 313, 314, 315 and 316 that will be described afterwards are formed at second substrate 102. The configuration of the fluid circuits (grooves) formed at opposite sides of second substrate 102 will be described in detail hereinafter.

As used herein, "two layers" implies that fluid circuits are provided at two different positions in the thickness direction of the microchip. The first and second fluid circuits may be communicated with each other via one or more through holes penetrating in the thickness direction, formed in the second substrate.

The microchip includes fluid circuits of two layers, increase in the scale of integration and density of fluid circuits is allowed. Thus, fluid circuits that allows fluid treatment of a more complex level can be formed. Moreover, the substrate area (microchip area) can be reduced by employing fluid circuits of two layers. Thus, the flatness of each substrate at the time of uniting the substrates can be ensured, leading to the likelihood of obtaining pressure evenness over the entire substrate. Therefore, welding failure can be prevented or suppressed.

Figure 2B:
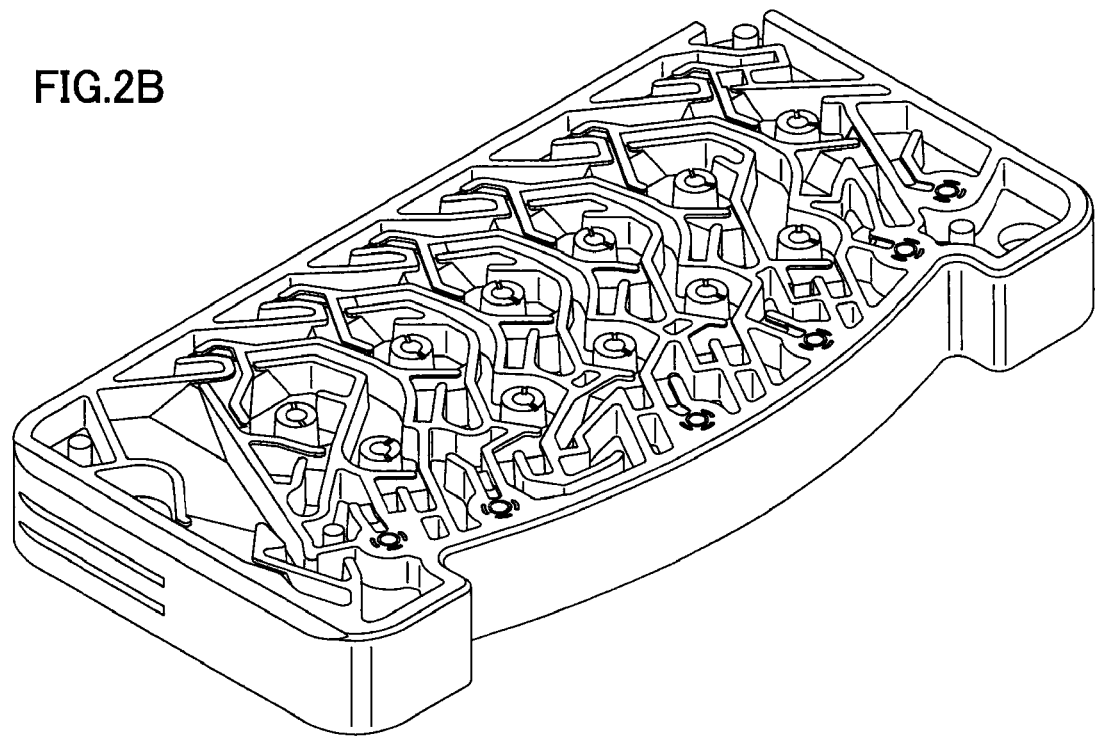

FIGS. 2A and 2B are perspective views of fluid circuits (grooves) formed at second substrate 102, the former representing the fluid circuits formed at the surface of second substrate 102 facing first substrate 101 (hereinafter, also simply referred to as "upper side"), and the later representing the fluid circuits formed at the surface of second substrate 102 facing third substrate 103 (hereinafter, also simply referred to as "lower side"). Namely, FIGS. 2A and 2B represent the first fluid circuit and the second fluid circuit, respectively. As shown in FIGS. 2A and 2B, second substrate 102 has grooves formed at the surface, and through holes penetrating in the thickness direction, which constitute respective sites where a specimen, liquid reagent, or mixture thereof is treated, and minute channels appropriately connecting these sites.

Figure 3:
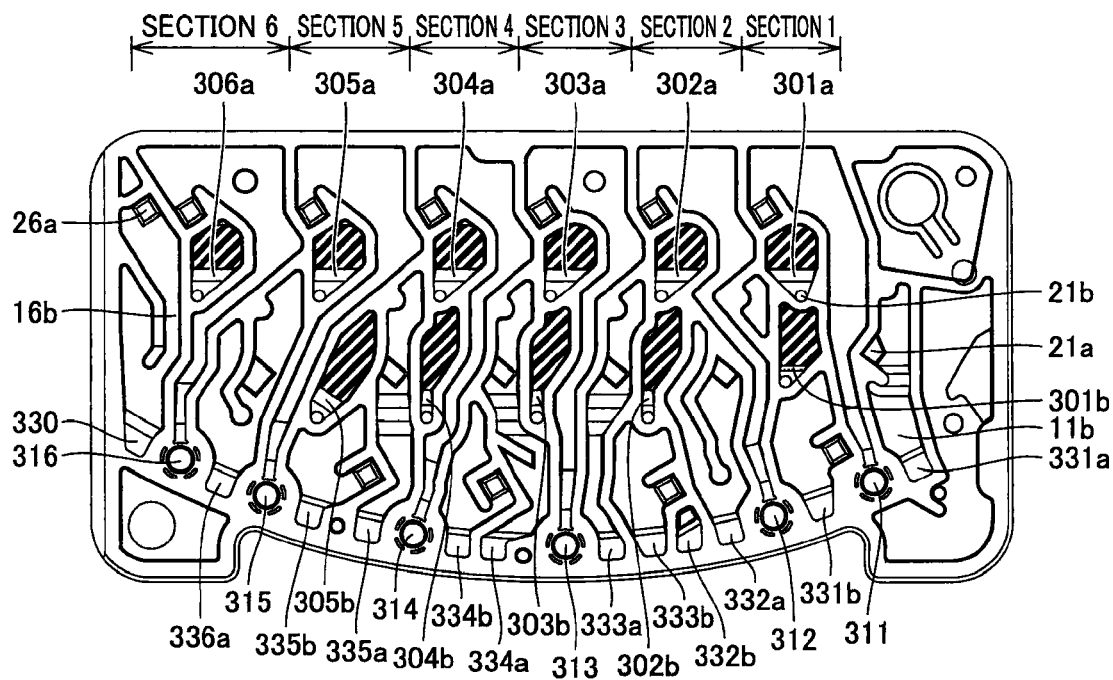
FIGS. 3 and 4 are a top view and a bottom view, respectively, of an example of a second substrate of a microchip of the present invention.
Figure 4:
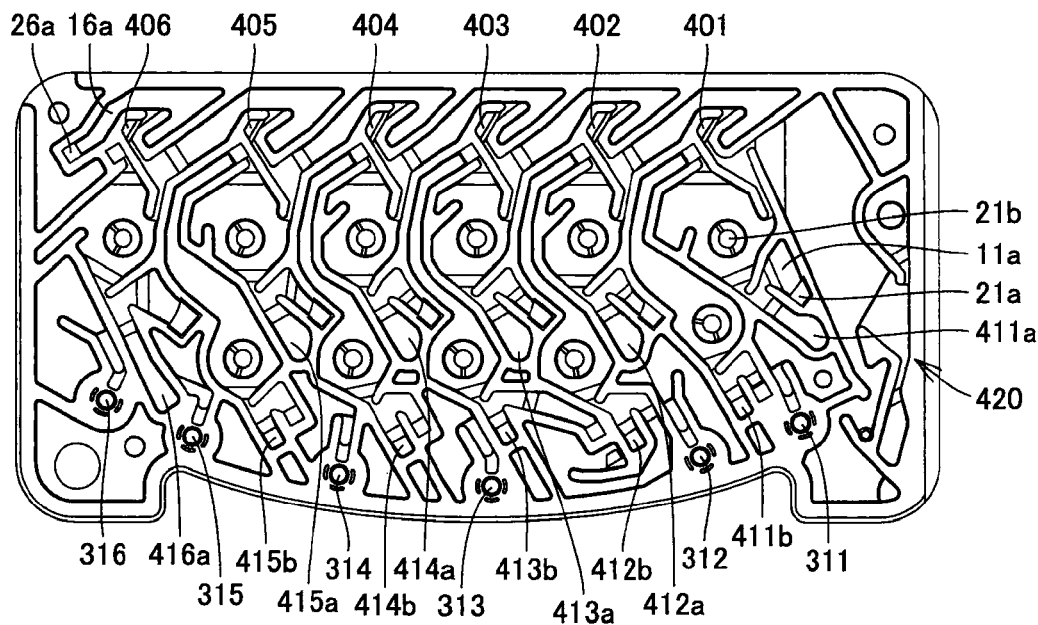

FIGS. 3 and 4 represent a top view and bottom view, respectively, of second substrate 102, the former corresponding to the upper side fluid circuits and the latter corresponding to the lower side fluid circuits, of second substrate 102. In FIG. 4, the lower side fluid circuits of the second substrate is illustrated in a mirror-reversed manner for the sake of convenience to identify the corresponding relationship with the upper side fluid circuits of FIG. 3. Microchip 100 of the present embodiment is a multi-test chip that allows examination and/or analysis of six items for one specimen. The fluid circuits are divided into six sections (sections 1-6 in FIG. 3) to allow examination and analysis of six items. It is to be noted that the six sections are connected with each other at the region where the specimen quantification unit is located (upper region of lower side fluid circuits). One or two liquid reagent receptacle units in which a liquid reagent is stored are provided for each section. In FIG. 3, a total of eleven liquid reagent receptacle units 301a, 301b, 302a, 302b, 303a, 303b, 304a, 304b, 305a, 305b and 306a are shown. The specimen introduced through specimen inlet 120 shown in FIG. 1 has the hematocyte component separated and removed, distributed to each section and quantified, mixed with one or two types of liquid reagents that is quantified individually in each section, and then guided to detection units 311, 312, 313, 314, 315 and 316. The mixture introduced into the detection unit of each section is subjected to optical measurement such as being irradiated with light at the detection unit from, for example, a direction substantially perpendicular to the surface of microchip 100, and measuring the transmissivity of the transmitted light, which is used for the detection of a certain component in the mixture. The series of treatments is effected by applying centrifugal force with respect to microchip 100 in an appropriate direction so that a liquid reagent, specimen or mixture thereof is appropriately and sequentially distributed to each site in the two layers of fluid circuits located at each section. Application of centrifugal force to microchip 100 can be effected by, for example, placing microchip 100 in a centrifuge that has a mounting portion for microchip 100.

At each of the aforementioned sections, a specimen quantification unit for quantifying the specimen (a total of six specimen quantification units 401, 402, 403, 404, 405 and 406 in FIG. 4) and a liquid reagent quantification unit for quantifying the liquid reagent (a total of eleven liquid reagent quantification units 411a, 411b, 412a, 412b, 413a, 413b, 414a, 414b, 415a, 415b and 416a in FIG. 4) are provided in the lower side fluid circuits. Each specimen quantification unit is connected in series by a channel (refer to FIG. 4).

As shown in FIG. 3, microchip 100 of the present invention includes an overflow specimen storage unit 330 to store a specimen overflowing from the specimen quantification unit during quantification, and overflow reagent storage units 331a, 331b, 332a, 332b, 333a, 333b, 334a, 334b, 335a, 335b and 336a to store a liquid reagent overflowing from the liquid reagent quantification unit. Overflow specimen storage unit 330 is connected with specimen quantification unit 406 via a channel 16a (refer to FIG. 4), a through hole 26a penetrating in the thickness direction, and a channel 16b (refer to FIG. 3). Each overflow reagent storage unit is connected with a corresponding liquid reagent quantification unit via a channel and a through hole. In section 1, for example, liquid reagent quantification unit 411a to quantify the liquid reagent stored in liquid reagent receptacle unit 301a is connected with overflow reagent storage unit 331a that stores the overflowing liquid reagent via a channel 11a (refer to FIG. 4), a through hole 21a penetrating in the thickness direction, and a channel 11b (refer to FIG. 3). The same applies to other overflow reagent storage units.

By detecting the absence or presence of overflowing liquid at a relevant overflow specimen storage unit and overflow reagent storage unit (hereinafter, also generically referred to as "overflow liquid storage unit") in microchip 100, identification can be readily made as to whether a specimen and liquid reagent is reliably distributed to a specimen quantification unit and liquid reagent quantification unit, representatively by means of centrifugal operation, and the relevant specimen quantification unit or liquid reagent quantification unit is filled with a specimen or liquid reagent. Namely, detection of the presence of overflow liquid at the overflow liquid storage unit guarantees that the specimen or liquid reagent at the specimen quantification unit or liquid reagent quantification unit has been properly quantified. Accordingly, the reliability of the examination and/or analysis on a specimen is improved. If an error in quantification is detected, determination can be made to not employ the obtained examination and/or analysis data. An error in quantification includes the case where a specimen or liquid reagent is not introduced into a specimen quantification unit or liquid reagent quantification unit due to an erroneous operation at the device, the case where a specimen or liquid reagent that should be quantified is not quantified due to evaporation of the liquid reagent, insufficient introduction of the specimen due to an erroneous manipulation by the user, a defect in uniting substrates together in the microchip fabrication procedure, and the like.

The method of detecting whether an overflow specimen or liquid reagent is present or not in an overflow liquid storage unit preferably includes, though not particularly limited to, the method of directing light from the side of first substrate 101 that is a transparent substrate towards the relevant overflow liquid storage unit, and measuring the intensity of reflected light thereof. The light to be employed is not particularly limited, and may be monochromatic light (for example, laser beam) having a wavelength of 400 to 1000 nm, for example, or mixed light of white light. The intensity of reflected light can be measured using a commercially-available reflection sensor.

The method of detecting the absence or presence of overflow liquid according to measurement of the intensity of reflected light basically includes the steps of obtaining the ratio of the intensity of reflected light identified by directing light from the first substrate side to the overflow liquid storage unit before overflow liquid is introduced into the overflow liquid storage unit to the intensity of reflected light identified by directing light to the overflow liquid storage unit from the first substrate side after a specimen or liquid reagent is introduced into the specimen quantification unit or liquid reagent quantification unit. When the ratio (reflected light intensity after introduction/reflected light intensity before introduction) is lower than 1 (i.e. the intensity of reflected light after introduction is lower), determination is made that overflow liquid is present in the overflow liquid storage unit. The measurement of the intensity of reflected light before introduction of overflow liquid may be skipped in the case where fabrication variation among microchips is small so that the intensity of reflected light before introduction of overflow liquid is assumed to be substantially constant among microchips.

Figure 5A:
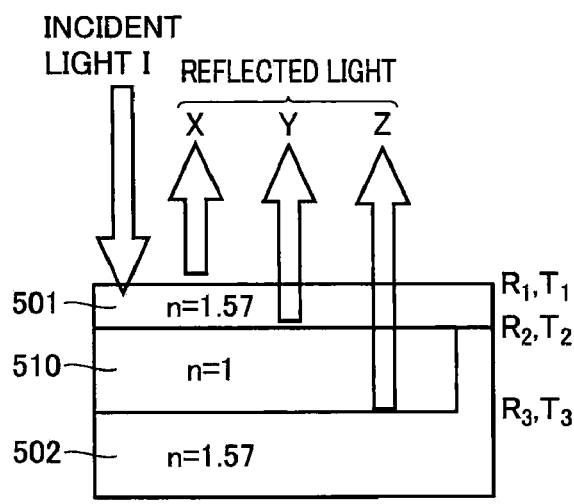
FIGS. 5A and 5B are diagrams to describe the relationship between the intensity of incident light and the intensity of reflected light before and after introduction of the overflow liquid in the overflow liquid storage unit.
Figure 5B:
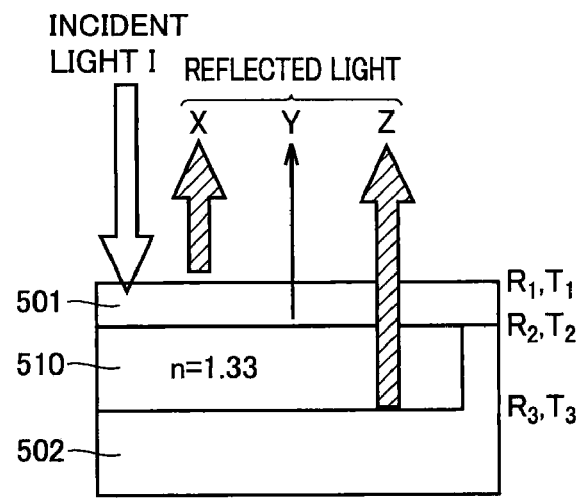

FIGS. 5A and 5B are diagrams to describe the relationship between the intensity of incident light and reflected light before and after overflow liquid is introduced into the overflow liquid storage unit. FIGS. 5A and 5B corresponds to the case before introduction and after introduction, respectively. The intensity of reflected light is represented by the following equation (1):

$$\text{Reflected light intensity} = R_1 I + \frac{T_1^2 R_2}{1 - R_1 R_2} I + \frac{T_1^2 T_2^2}{1 - R_1 R_2} R_3 I \quad (1)$$

where $R_1$, $R_2$ and $R_3$ are the light reflectivity and $T_1$, $T_2$ and $T_3$ are the light transmissivity at the surface of a first substrate 501, at the interface between first substrate 501 and an overflow liquid storage unit 510, and at the interface between overflow liquid storage unit 510 and a second substrate 502, and $T_4$ is the light transmissivity of the liquid (or air) in overflow liquid storage unit 510, when the refractive index of first and second substrates 501 and 502 is 1.57, and the light beam of incident intensity I is applied from the side of first substrate 501.

The first term at the right side in equation (1) corresponds to the intensity originating from reflected light X shown in FIGS. 5A and 5B (light reflected from the surface of first substrate 501), the second term corresponds to the intensity originating from reflected light Y (reflection from the interface between first substrate 501 and overflow liquid storage unit 510), and the third term corresponds to the intensity originating from reflected light Z (reflection from the interface between overflow liquid storage unit 510 and second substrate 502).

In the case where there is no overflow liquid and only air is present in overflow liquid storage unit 510 (the event of FIG. 5A), $R_1$ is calculated to be approximately 0.05. Moreover, $R_1 = R_2 = R_3$ is established, and therefore $T_1 = T_2 = 0.95$. By inserting this into the right side of equation (1), reflected light intensity=$2.72 \times R_1 I$ is obtained.

In the case where water (refractive index 1.33), for example, is introduced in overflow liquid storage unit 510 (the event of FIG. 5B), $R_2$ is calculated to be 0.0068 (therefore, $T_2 = 0.9932$). By inserting this into the right side of equation (1) similarly, reflected light intensity=$1.24 \times R_1 I$ is obtained. The aforementioned calculation results indicate that the ratio of the reflected light intensity after introduction/reflective light intensity before introduction is 0.45. In view of the reflected light intensity being degraded by the introduction of overflow liquid in overflow liquid storage unit 510 (in the present example of calculation, a reduction of 55%), identification of the absence or presence of overflow liquid can be made readily by identifying such reduction in the reflected light intensity. In practice, a microchip based on a thermoplastic resin having the refractive index set forth above was produced and monochromatic light having a wavelength of 800 nm was applied, resulting in the ratio of 0.425 with respect to the reflected light intensity before and after introduction of water.

In the case where an opaque substrate (for example, black substrate) is employed for second substrate 502, the third term in equation (1) (reflectivity at the interface between overflow liquid storage unit 510 and second substrate 502) is substantially 0. Therefore, the difference in the reflected light intensity value before and after overflow liquid introduction will depend only on the difference in the intensity of the second term (reflectivity from the interface between first substrate 501 and overflow liquid storage unit 510). Since the intensity of the second term does not depend upon the transparency/non-transparency of the overflow liquid, the absence or presence of overflow liquid can be identified regardless of whether the overflow liquid is opaque or not in the case where an opaque substrate (for example, black substrate) is employed for second substrate 502. In contrast, the usage of a transparent substrate for second substrate 502 will afford a contribution to the third term in equation (1), rendering the measurement of the reflected light intensity complicated. This will induce the events set forth below. Firstly, there may be a case where a constant reflected light intensity cannot be obtained for a plurality of overflow liquid storage units since the reflected light intensity will vary depending upon the transmissivity of the fluid (overflow liquid) stored in an overflow liquid storage unit (the reflected light intensity will depend upon $T_4$ as a result of the contribution of the third term, as indicated in equation (1)). Therefore, a threshold value for determining the absence or presence of overflow liquid must be defined for each type of liquid stored in the overflow liquid storage unit. Furthermore, when a transparent substrate is employed for second substrate 502, the reflected light intensity may vary depending upon the thickness (depth) of the overflow liquid storage unit even if the liquid that is the target of detection is opaque having a constant transmissivity. Therefore, the threshold value used for determining the absence or presence of fluid liquid must be determined according to, not only the type of the stored liquid, but also the thickness (depth) of the overflow liquid storage unit. In the case where an opaque substrate (for example, black substrate) is employed for second substrate 502, a constant reflected light intensity value can be obtained even if an opaque liquid is stored in the overflow liquid storage unit. Therefore, the absence or presence of liquid in an overflow liquid storage unit can be identified using a threshold value identical to that used in the case of determining the absence or presence of the overflow liquid for a transparent liquid.

The technique of identifying whether liquid is present or not (or absent or not) based on measurement of the reflected light intensity set forth above can be applied to other sites of microchip 100, in addition to the overflow liquid storage unit. For example, light can be directed to a liquid reagent receptacle unit before actual usage of microchip 100 and measure the reflected light intensity to allow identification of whether a liquid reagent is present or not in a liquid reagent receptacle unit. Accordingly, the failure of a liquid reagent not being stored in the liquid reagent receptacle unit due to flow out by shock or evaporation during transportation can be identified. Moreover, light can be directed to a specimen quantification unit, a liquid reagent quantification unit, a mixing unit in which a specimen and liquid reagent are mixed, or the like, and measure the intensity of reflected light therefrom to reliably identify whether a specimen, liquid reagent, or mixture thereof is present in a relevant quantification unit or mixing unit. This can guarantee that a predetermined treatment through application of centrifugal force is reliably carried out. In addition, light can be directed to a liquid reagent quantification unit, mixing unit, and detection unit during the stage prior to the blood plasma separation and liquid reagent quantification procedure (for example, immediately before actual use of microchip 100), and measure the intensity of reflected light therefrom. Accordingly, identification can be made as to whether liquid reagent or a specimen is present at these sites. Thus, the event of an error in which a liquid reagent or specimen has run to an undesired site due to liquid leakage caused by a fall during transportation or fabrication failure can be detected.

As another method of detecting whether an overflow specimen or liquid reagent is present in an overflow liquid storage unit, there is known the method of directing light to the overflow liquid storage unit and measuring the transmitting light thereof, as disclosed in the aforementioned U.S. Pat. No. 5,590,052. The above-described method of measuring reflected light is preferable, as compared to the method of measuring transmitted light, as will be described hereinafter.

(i) An amount of liquid corresponding to the thickness of the microchip is not required. Therefore, detection with a minute amount is allowed.

(ii) The method of measuring reflected light allows the usage of an opaque substrate, since transparency is required only at the substrate of the light incident side (for example, the second substrate in the embodiment set forth above may be an opaque substrate).

(iii) Fabrication of a region through which light passes (optical region) is facilitated, and the configuration of the optical region can be rendered simple. In other words, the optical region does not have to be formed spanning over both the layers of fluid circuits, when provided in the microchip, as in the present embodiment. Accordingly, the degree of freedom in designing can be increased. In addition, the area occupied by the optical region can be reduced. In contrast, if the method of measurement based on transmitted light is employed, the optical region must be formed at both layers. Therefore, the area occupied by the optical regions will be increased, and an additional step of design registration will be required for the positioning of the optical regions.

(iv) In the case where an opaque substrate (for example, black substrate) is employed for second substrate 502 as set forth above, a constant reflected light intensity value can be obtained even in the case where opaque liquid is stored in the overflow liquid storage unit. Therefore, the absence or presence of liquid in the overflow liquid storage unit can be detected using a threshold value identical to that used in the case of determining the absence or presence of the overflow liquid for a transparent liquid.

The total of eleven overflow reagent storage units corresponding to respective liquid reagents and one overflow specimen storage unit in microchip 100 of the present embodiment are all preferably formed in the first fluid circuit (upper side fluid circuits) (refer to FIG. 3). By forming all overflow liquid storage units at one side fluid circuits, microchip 100 does not have to be turned over at the time of measuring the reflected light intensity, allowing the detection of the absence or presence of overflow liquid at all the storage units readily and rapidly. Moreover, the overflow liquid storage units are preferably arranged on the circumference of the same circle in one side fluid circuits formed at the surface of the second substrate (refer to FIG. 3). This circle is preferably a circle about the center of the circular path along with microchip 100 moves such that centrifugal force is exerted to microchip 100. Specifically, since microchip 100 is generally mounted on a rotatable circular stage of a centrifuge and subjected to centrifugal force, it can be said that the circle about the center of the circular path is a circle about the revolution center of the circular stage. The arrangement of all the overflow liquid storage units on the circumference of the same circle is advantageous in that the light reflected intensity can be measured by directing light from a fixed light source (an apparatus having the light source and reflected light intensity measurement means integrally formed) while the circular stage on which microchip 100 is mounted is rotated to sequentially locate an overflow liquid storage unit on the optical axis of the reflected light. Thus, measurement of reflected light intensity can be carried out conveniently and rapidly.

Referring to FIG. 1, a recess 130 (a total of 12 recesses) is formed on the surface of first substrate 101, at a location immediately above an overflow liquid storage unit in the first fluid circuit (upper side fluid circuits). The formation of such a recess can prevent reduction in the intensity of reflected light, caused by attachment of a fingerprint, before the overflow liquid is introduced into the overflow liquid storage unit. Although the measurement of the reflected light intensity prior to introduction of overflow liquid can be skipped in the case where the intensity of reflected light before introduction of overflow liquid can be assumed to be substantially constant among microchips 100, there is a possibility of erroneous determination of the absence or presence of overflow liquid when the reflected light intensity is actually reduced due to attachment of a finger print. The depth of recess 130 is, but not particularly limited to, approximately 1.1 mm at most, for example, when the thickness of first substrate 101 is 1.6 mm.

In microchip 100 of the present embodiment, a recess is similarly formed (a total of six) on the surface of first substrate 101 at a location immediately above the optical measurement cuvette in the first fluid circuit from the standpoint of the same reason set forth above. However, such a recess is dispensable in the present invention.

An example of fluid treatment based on microchip 100 of the present embodiment will be described hereinafter with reference to FIGS. 6A to 12B. These drawings represent the state of the liquid (specimen, liquid reagent, and mixture thereof) at the top face of second substrate 102 (the surface facing a first substrate) and at the bottom face (the surface facing the third substrate) of second substrate 102 during respective procedures in the fluid treatment. FIGS. 6A, 7A, 8A, 9A, 10A, 11A and 12A represent the state of the liquid at the top face of the second substrate (first fluid circuit) whereas FIGS. 6B, 7B, 8B, 9B, 10B, 11B and 12B represent the state of the liquid at the bottom face of the second substrate (second fluid circuit). Likewise with FIG. 4, the lower side fluid circuits of second substrate 102 in FIGS. 6B, 7B, 8B, 9B, 10B, 11B and 12B is illustrated in a mirror-reversed manner to readily identify the corresponding relationship with the upper side fluid circuits in FIGS. 6A, 7A, 8A, 9A, 10A, 11A and 12A. Although the description set forth below is based on the fluid treatment at the fluid circuits in section 1, it is to be understood that a similar treatment is carried out at other sections by referring to the drawings. Further, although the following description is based on the case where the specimen is whole blood (as defined before, the blood plasma component separated from whole blood may also be referred to as "specimen" hereinafter), the type of specimen is not limited thereto.

(1) Hematocyte Separation and Liquid Reagent Quantification Procedure

Figure 6A:
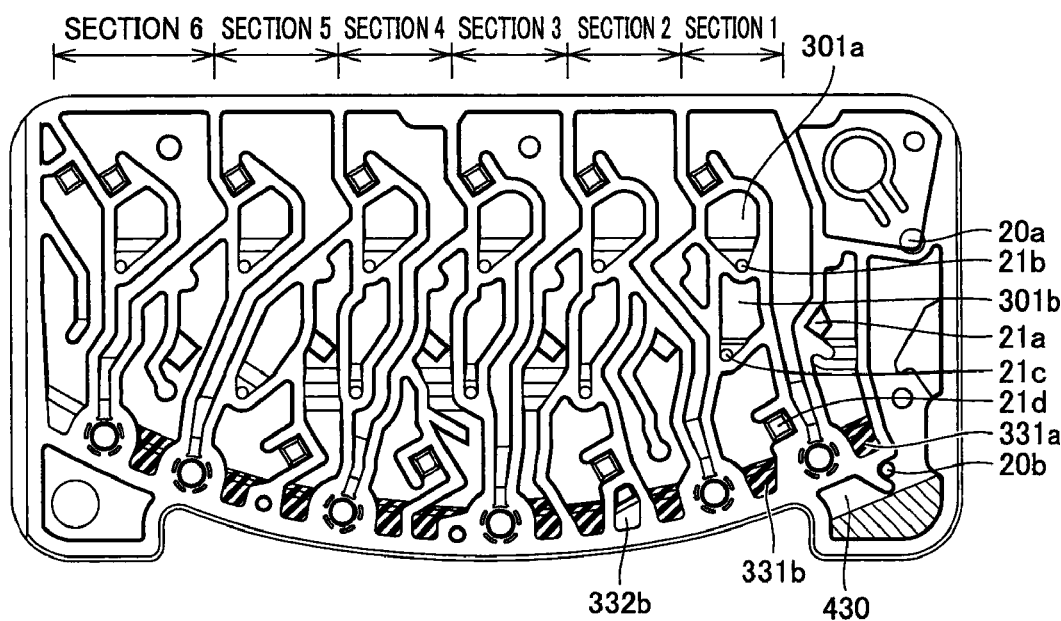
FIGS. 6A and 6B represent the state of the liquid at the top face of the second substrate (the surface facing the first substrate) and at the bottom face of the second substrate (the surface facing the third substrate), respectively, in a hematocyte separation and liquid reagent quantification procedure.
Figure 6B:
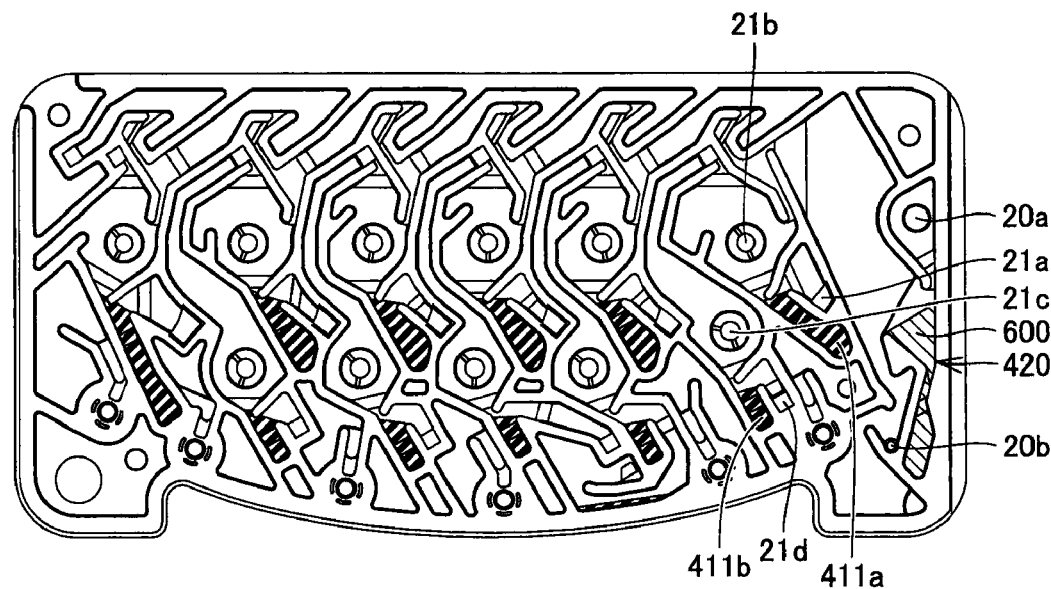
Figure 7A:
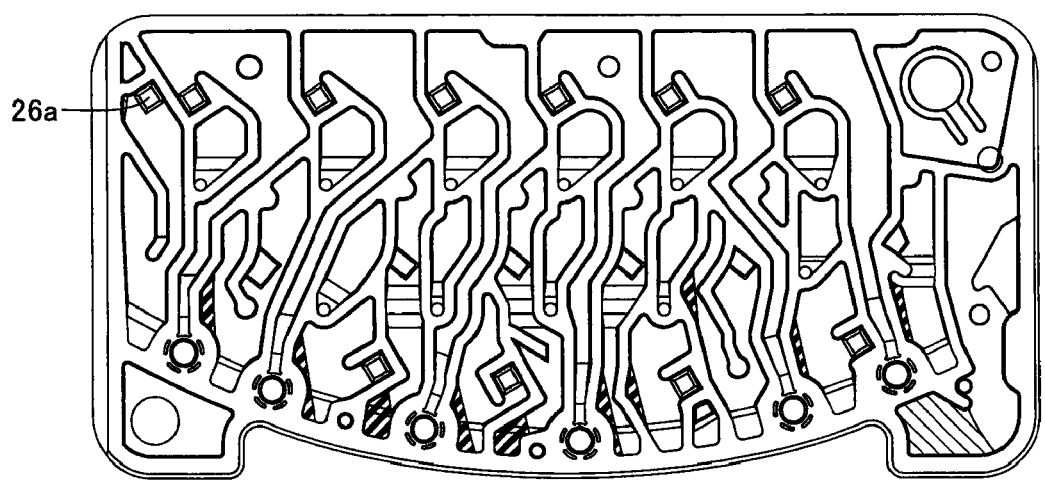
FIGS. 7A and 7B represent the state of the liquid at the top face of the second substrate (the surface facing the first substrate) and at the bottom face of the second substrate (the surface facing the third substrate), respectively, in a specimen quantification procedure.
Figure 7B:
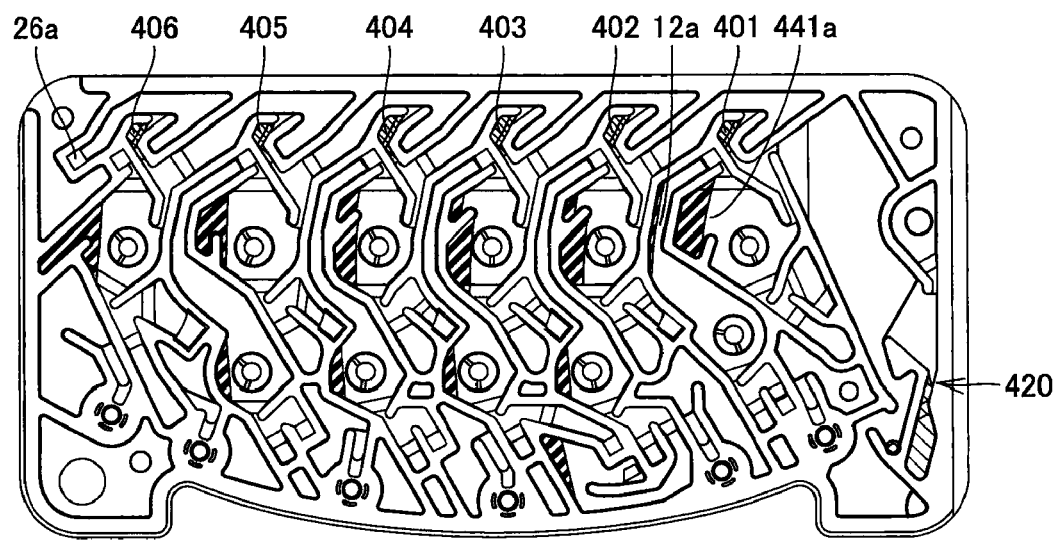
Figure 8A:
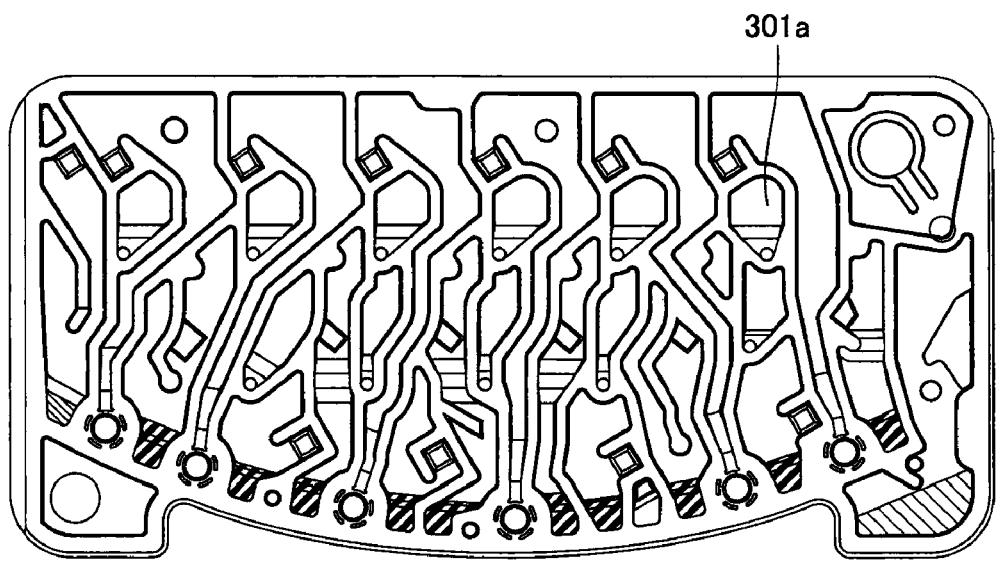
FIGS. 8A and 8B represent the state of the liquid at the top face of the second substrate (the surface facing the first substrate) and at the bottom face of the second substrate (the surface facing the third substrate), respectively, in a first step of a first mixture procedure.
Figure 8B:
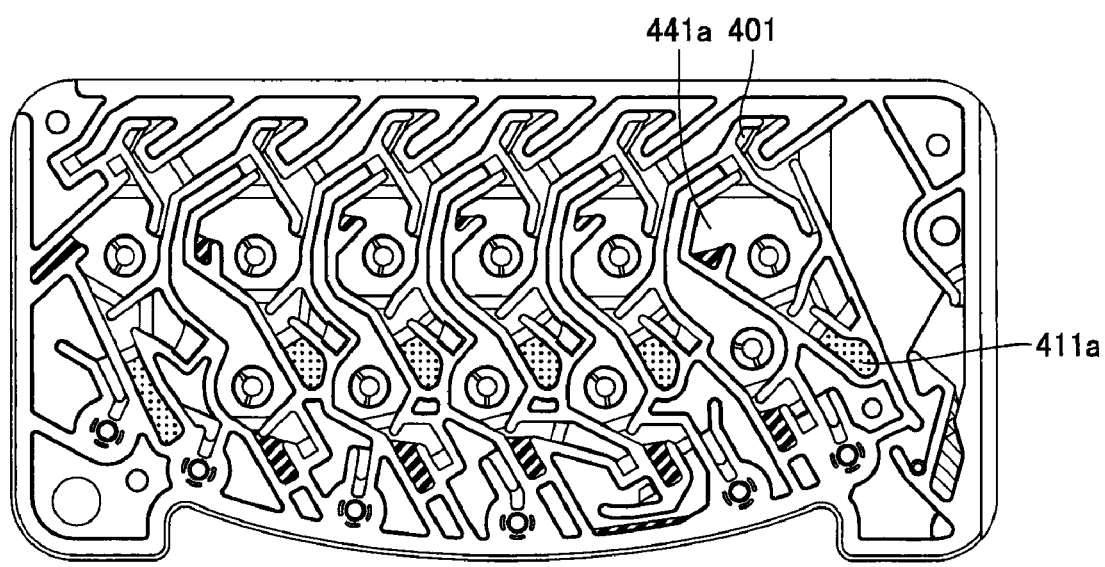

In the present procedure, centrifugal force is applied in the downward direction in FIGS. 6A and 6B (hereinafter, simply referred to "downward"; the same applies for FIGS. 7A, 7B to FIGS. 12A, 12B, as well as to other directions) with respect to the microchip in the state indicated in FIGS. 3 and 4. Accordingly, the whole blood introduced through specimen inlet 120 (refer to FIG. 1) of first substrate 101 is delivered to the lower side fluid circuits via a through hole 20a to enter hematocyte separation unit 420 (refer to FIG. 6B). Whole blood 600 introduced into hematocyte separation unit 420 is subjected to centrifugation thereat to be divided into blood plasma components (upper layer) and hematocyte components (lower layer). The whole blood overflowing from hematocyte separation unit 420 moves to the upper side fluid circuits via a through hole 20b to be stored in a waste reservoir 430 (refer to FIG. 6A). By this downward application of centrifugal force, the liquid reagents in liquid reagent receptacle units 301a and 301b are shifted via through holes 21b and 21c to reach liquid reagent quantification units 411a and 411b for quantification (refer to FIG. 6B). The liquid reagent overflowing from each liquid reagent quantification unit runs via through holes 21a and 21b to be stored in overflow reagent storage units 331a and 331b in the upper side fluid circuits (refer to FIG. 6A). At this stage, a liquid reagent is present in all overflow reagent storage units except for overflow reagent storage unit 332b in the case where there is no fault in the liquid amount in association with the liquid reagent. The presence of a liquid reagent may be confirmed by directing light to the liquid reagent receptacle unit, prior to the present procedure, and measuring the intensity of reflected light therefrom. In addition, by directing light to the liquid reagent quantification unit, mixing unit, and detection unit, and measure the intensity of reflected light therefrom at the stage prior to the hematocyte separation and liquid reagent measurement procedure, the absence or presence of a liquid reagent and/or specimen at respective sites may be identified.

(2) Specimen Quantification Procedure

Then, leftward centrifugal force is applied. In response, the blood plasma component separated at hematocyte separation unit 420 is introduced into specimen quantification unit 401 (also introduced simultaneously to specimen quantification units 402, 403, 404 as well as to 405 and 406) to be quantified (refer to FIG. 7B). The plasma component overflowing from the quantification unit is delivered to the upper side fluid circuits via a through hole 26a (refer to FIG. 7A). This leftward centrifugal force causes the liquid reagent in liquid reagent quantification unit 411a to move to mixing unit 441a, and the liquid reagent in liquid reagent quantification unit 411b to channel 12a. At this stage, the presence of blood plasma components at the specimen quantification unit may be identified by directing light to each specimen quantification unit and measuring the intensity of reflected light therefrom.

(3) First Mixing Procedure

Figure 9A:
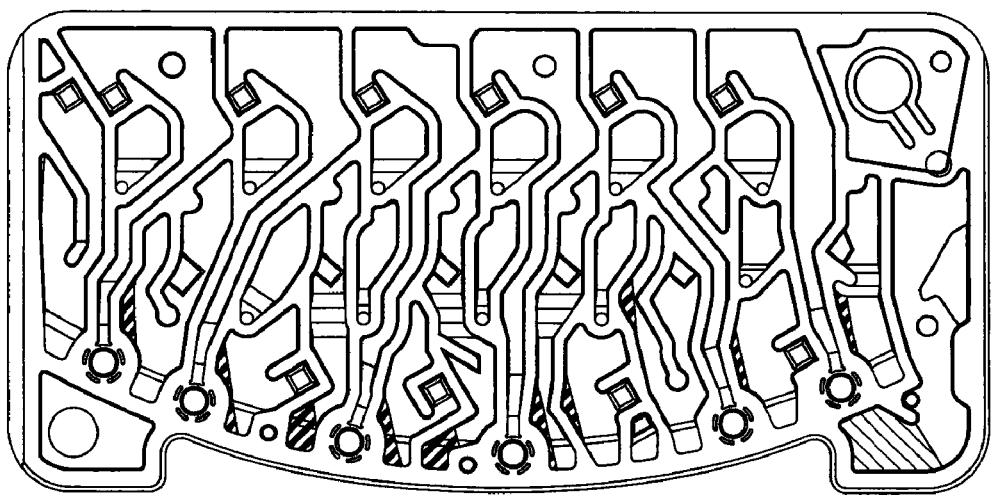
FIGS. 9A and 9B represent the state of the liquid at the top face of the second substrate (the surface facing the first substrate) and at the bottom face of the second substrate (the surface facing the third substrate), respectively, in a second step of the first mixture procedure.
Figure 9B:
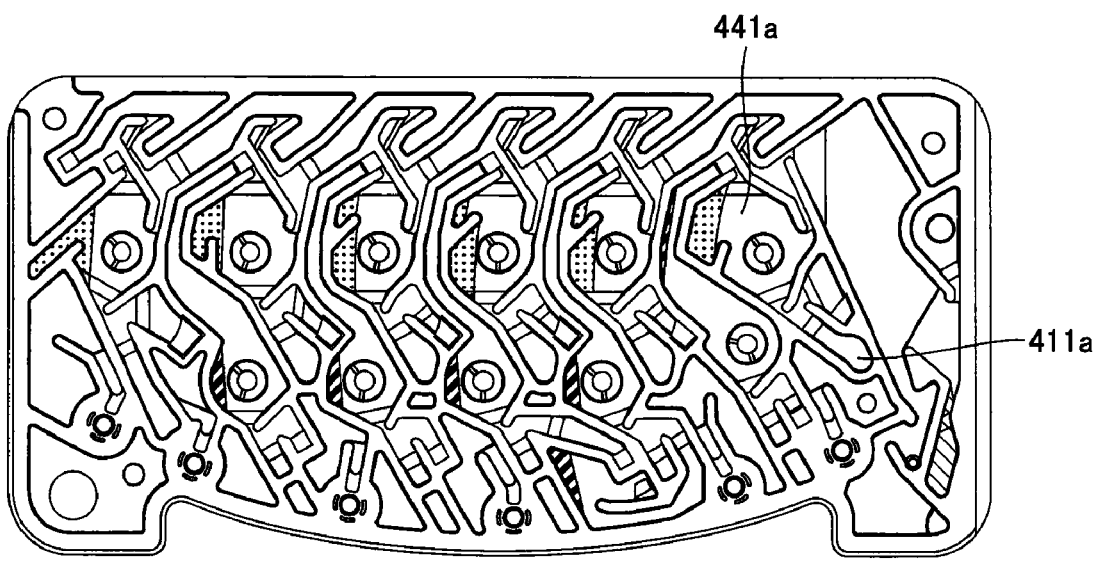
Figure 10A:
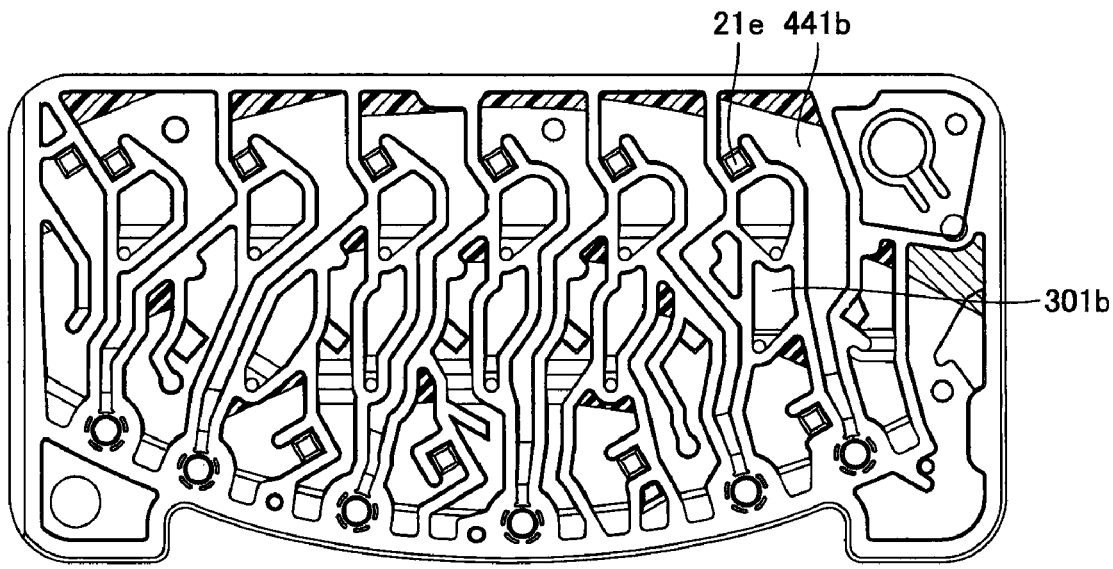
FIGS. 10A and 10B represent the state of the liquid at the top face of the second substrate (the surface facing the first substrate) and at the bottom face of the second substrate (the surface facing the third substrate), respectively, in a first step of a second mixture procedure.
Figure 10B:
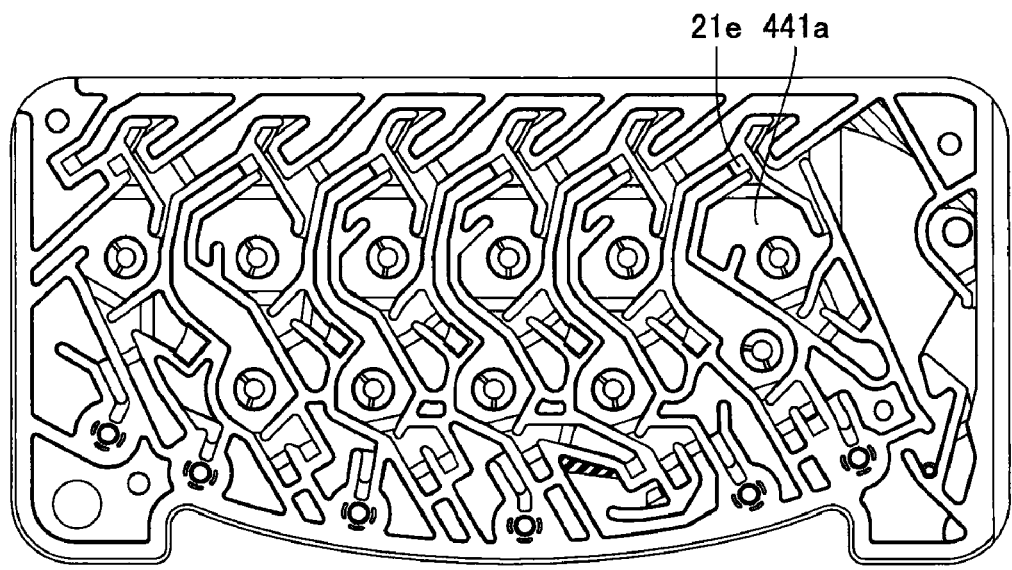

Then, downward centrifugal force is applied. In response, the quantified liquid reagent (liquid reagent stored in liquid reagent receptacle unit 301a) and the blood plasma component quantified at specimen quantification unit 401 are mixed at liquid reagent quantification unit 411a (refer to the first step in the first mixing procedure of FIG. 8B). At this stage, a liquid reagent remains in mixing unit 441a at the lower side fluid circuits. Presence of a mixture at the liquid reagent quantification unit may be identified at this stage by directing light to each liquid reagent quantification unit to measure the intensity of light reflected therefrom. Measurement of the intensity of reflected light from the overflow specimen storage unit at this stage allows early detection of a defect such as insufficient introduction of a specimen. Then, by applying leftward centrifugal force, the mixture is further mixed with the liquid reagent remaining in mixing unit 441a (refer to the second step in the first mixing procedure in FIG. 9B). Mixture is ensured by carrying out the first and second steps for a plurality of times, as necessary. Eventually, a state similar to that shown in FIGS. 9A and 9B is obtained.

(4) Second Mixing Procedure

Figure 11A:
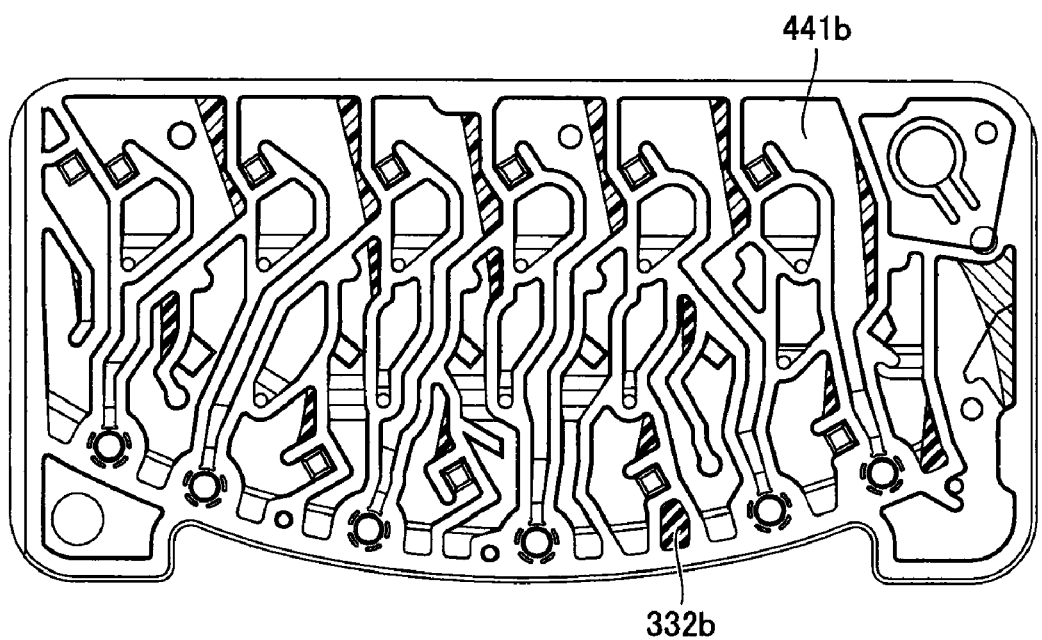
FIGS. 11A and 11B represent the state of the liquid at the top face of the second substrate (the surface facing the first substrate) and at the bottom face of the second substrate (the surface facing the third substrate), respectively, in a second step of the second mixture procedure.
Figure 11B:
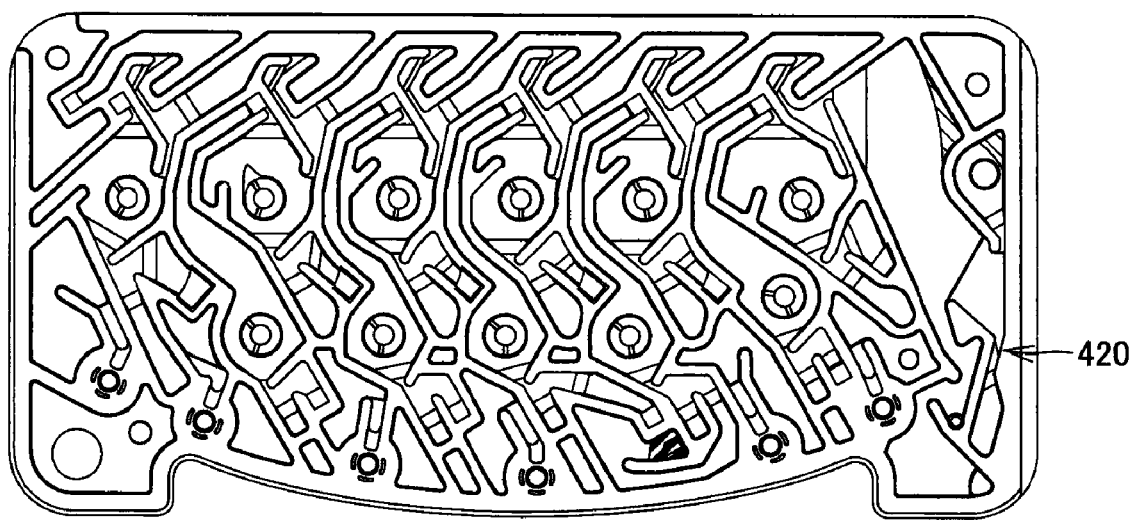
Figure 12A:
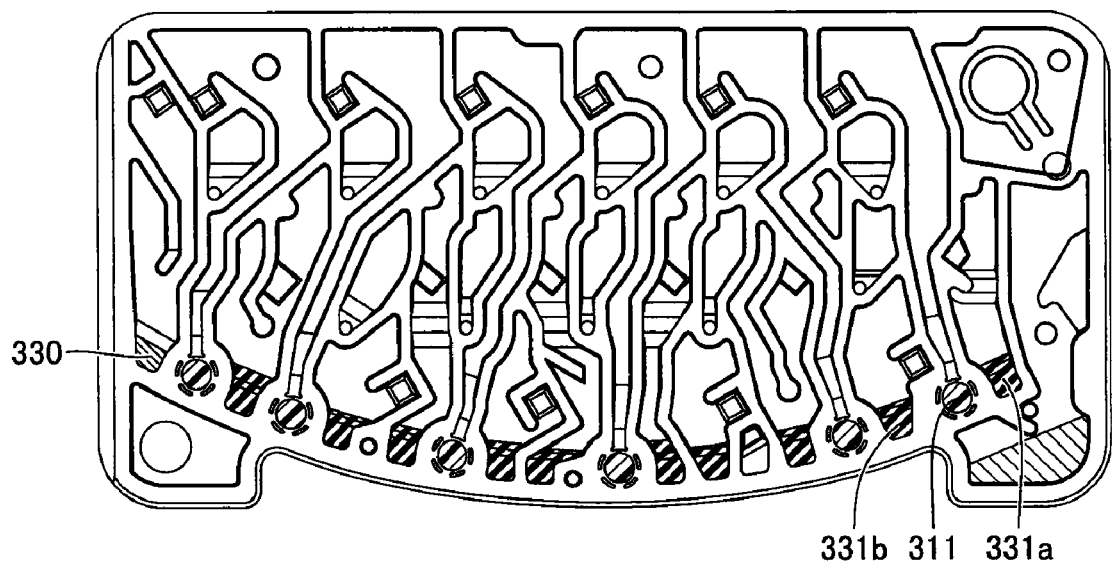
FIGS. 12A and 12B represent the state of the liquid at the top face of the second substrate (the surface facing the first substrate) and at the bottom face of the second substrate (the surface facing the third substrate), respectively, in a detection unit introduction procedure.
Figure 12B:
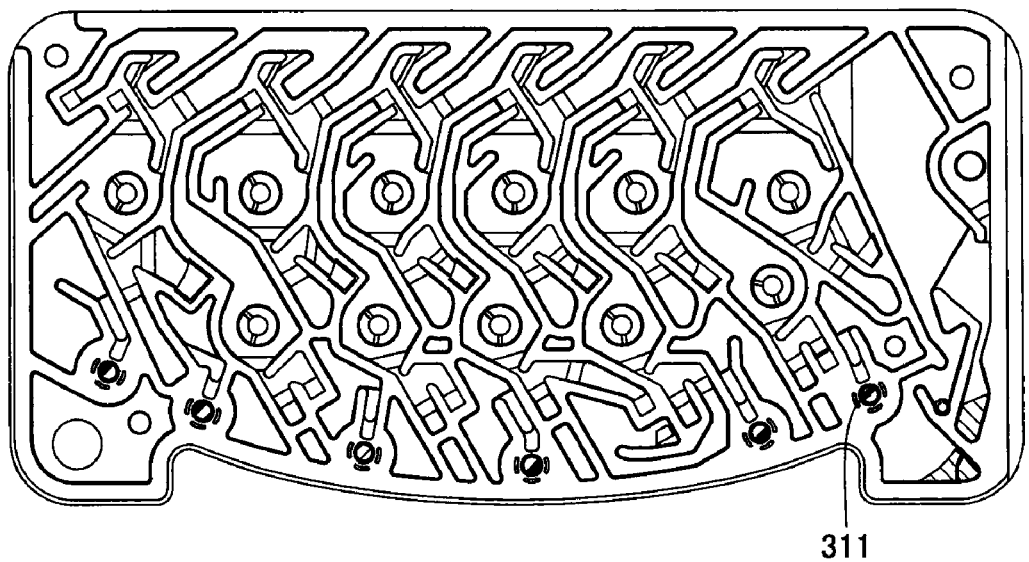

Then, upward centrifugal force is applied. In response, the mixture in mixing unit 441a reaches mixing unit 441b via a through hole 21e, whereas the other quantified liquid reagent (liquid reagent stored in liquid reagent receptacle unit 301b) reaches mixing unit 441b via a through hole 21e to be mixed together (refer to the first step in the second mixing procedure in FIG. 10A). Confirmation of the presence of mixture at the mixing unit can be made at this stage by directing light to each mixing unit and measuring the intensity of reflected light therefrom. Then, by applying rightward centrifugal force, the mixture is moved within mixing unit 441b, as shown in FIG. 11A, to promote the mixing (refer to the second step in the second mixing procedure in FIG. 11A). This rightward centrifugal force also causes the liquid reagent to be stored in overflow reagent storage unit 332b (refer to FIG. 11A). Mixture is ensured by carrying out these first and second steps a plurality of times, as necessary. Eventually, a state similar to that shown in FIGS. 11A and 11B is obtained.

(5) Detection Unit Introduction Procedure

Lastly, downward centrifugal force is applied. In response, the mixture is introduced into a cuvette (detection unit) 311 for optical measurement. The same applies to the other mixture (refer to FIGS. 12A and 12B). In addition, overflow reagent storage units 331a and 331b as well as overflow specimen storage unit 330 has a liquid reagent or specimen (blood plasma component) stored therein. The same applies to other overflow reagent storage units. The mixture in the optical measurement cuvette (detection unit) is subjected to optical measurement for the examination and analysis of the specimen (plasma component). Detection and the like of a certain component in the mixture is carried out by, for example, directing light from a direction substantially perpendicular to the surface of microchip 100 and measuring the transmitted light thereof. Furthermore, light is directed to the overflow specimen storage unit and each overflow reagent storage unit to measure the intensity of reflected light therefrom at this stage to confirm the absence or presence of the specimen or liquid reagent. Although this confirmation of the presence/absence of the specimen or liquid reagent does not have to be necessarily carried out at this stage, it is preferable to confirm the presence/absence of a specimen or liquid reagent after the detection unit introduction procedure for the sake of simplifying the operation since it is this stage when the specimen or liquid reagent should be stored in all the overflow specimen storage unit and overflow reagent storage units.

The method of uniting substrates together is not particularly limited. For example, the method of fusing at least one of the uniting faces of the substrates for welding (welding method), the method of attaching using an adhesive, and the like are known. The welding method includes the method of heating a substrate for welding, the method of directing a laser beam or the like to effect welding by the heat generated during light absorption, and the method of welding based on an ultrasonic wave can be cited.

The size of the microchip of the present invention may be set to, though not particularly limited to, several cm to approximately 10 cm in the vertical and horizontal directions, and several millimeters to several centimeters in thickness.

The material of each substrate set forth above constituting a microchip of the present invention includes, though not particularly limited to, an organic material such as polyethylene terephthalate (PET), polybutylene terephthalate (PBT), polymethylmethacrylate (PMMA), polycarbonate (PC), polystyrene (PS), polypropylene (PP), polyethylene (PE), polyethylenenaphthalate (PEN), polyalylate resin (PAR), acrylonitrile butadiene styrene resin (ABS), styrene-butadiene resin (styrene-butadiene copolymer), polyvinyl chloride resin (PVC), polymethyl pentene resin (PMP), polybutadiene resin (PBD), biodegradable polymer (BP), cycloolefin (COP), and poly dimethyl siloxane (PDMS), as well as an inorganic material such as silicon, glass, and quartz. In consideration of facilitating formation of fluid circuits, resin is preferable, and styrene-butadiene copolymer is more preferable. Styrene-butadiene copolymer has the property of both favorable transparency based on styrene, and favorable viscosity based on butadiene, and is advantageous in that the resin can be readily detached from the mold without breakage while maintaining the shape even in the case where the area of contact between the resin and mold is extremely large in order to form minute patterns.

In the case where the first substrate, second substrate and third substrate are to be united by welding such as laser welding, thermal welding, or ultrasonic welding, the melting point or glass transition point of the resin or resin composition constituting the second substrate is preferably higher than the melting point or glass transition point of the resin or resin composition constituting the second and third substrates. Accordingly, deformation of grooves on the second substrate during the uniting procedure can be prevented effectively.

Each of the first, second, and third substrates may be a transparent substrate, or an opaque substrate (colored substrate) such as a black substrate having the substrate base formed of resin, and adding black pigment such as carbon black into the resin. Preferably, an opaque substrate such as a black substrate is used for the second substrate that is located in the middle, and a transparent substrate is used for the first and third substrates that sandwich the second substrate. This allows optical measurement such as by directing light from a direction substantially perpendicular to the microchip surface to a site where a mixture of specimen and liquid reagent that is to be subjected to examination and/or analysis is stored (for example, optical measurement cuvette (detection unit)) and detecting the intensity of the transmitting light (transmissivity), as will be described afterwards.

The method of forming grooves (pattern grooves) constituting fluid circuits at the surface of the second substrate includes, though not particularly limited to, injection molding employing a mold of a transfer configuration, imprinting, and the like. In the case where the substrate is to be formed using an inorganic material, an etching method or the like can be employed.

The sites constituting the fluid circuits are not particularly limited to those in the microchip of FIG. 1. Each of the sites such as a liquid reagent receptacle unit to store a liquid reagent, a separation unit to extract a certain component from the specimen introduced into the fluid circuits, a specimen quantification unit to quantify a specimen, a liquid reagent quantification unit to quantify a liquid reagent, a mixing unit to mix a specimen and liquid reagent, an optical measurement cuvette (detection unit) to carry out examination and analysis (for example, detect or quantify a certain component in the mixture) on the obtained mixture may be one or more in number. The microchip of the present invention may include all or at least one of these exemplified sites. Furthermore, a site other than that set forth above may be included.

Figure 15:
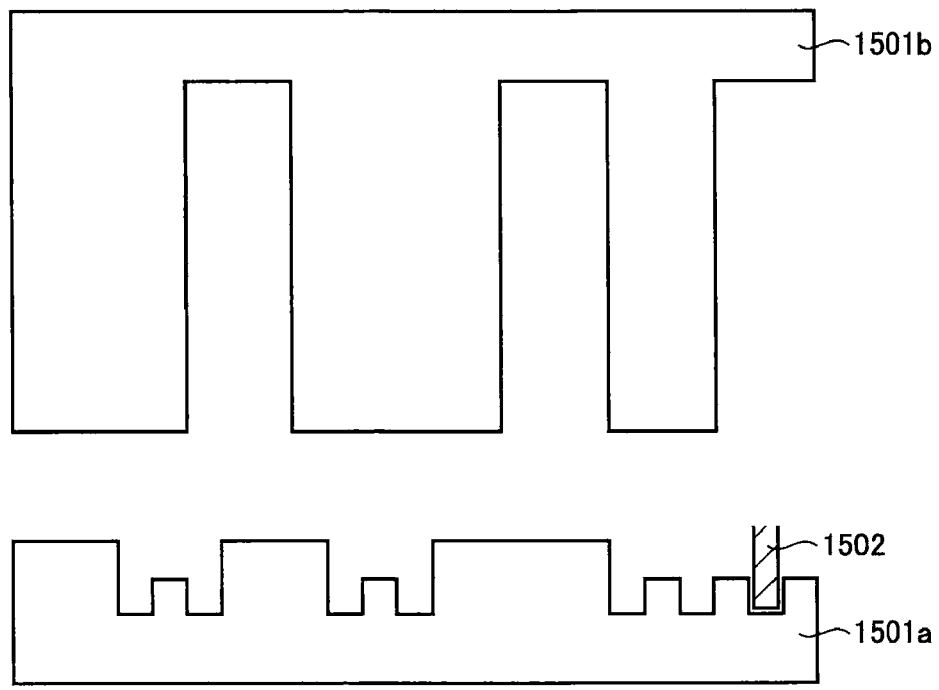
FIG. 15 is a schematic sectional view of a shape of a mold used to form a second substrate having a plurality of shallow grooves at one surface and deep grooves at another surface.
Figure 16:
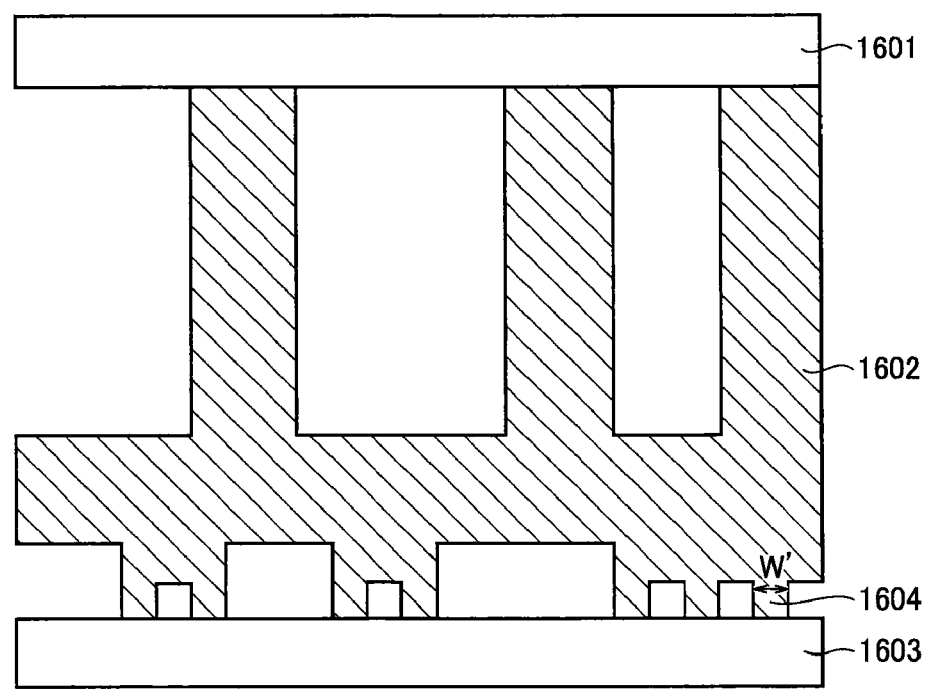
FIG. 16 is a schematic sectional view of a microchip of the present invention, produced based on a second substrate obtained from the mold of FIG. 15, a first substrate, and a third substrate.
Figure 17:
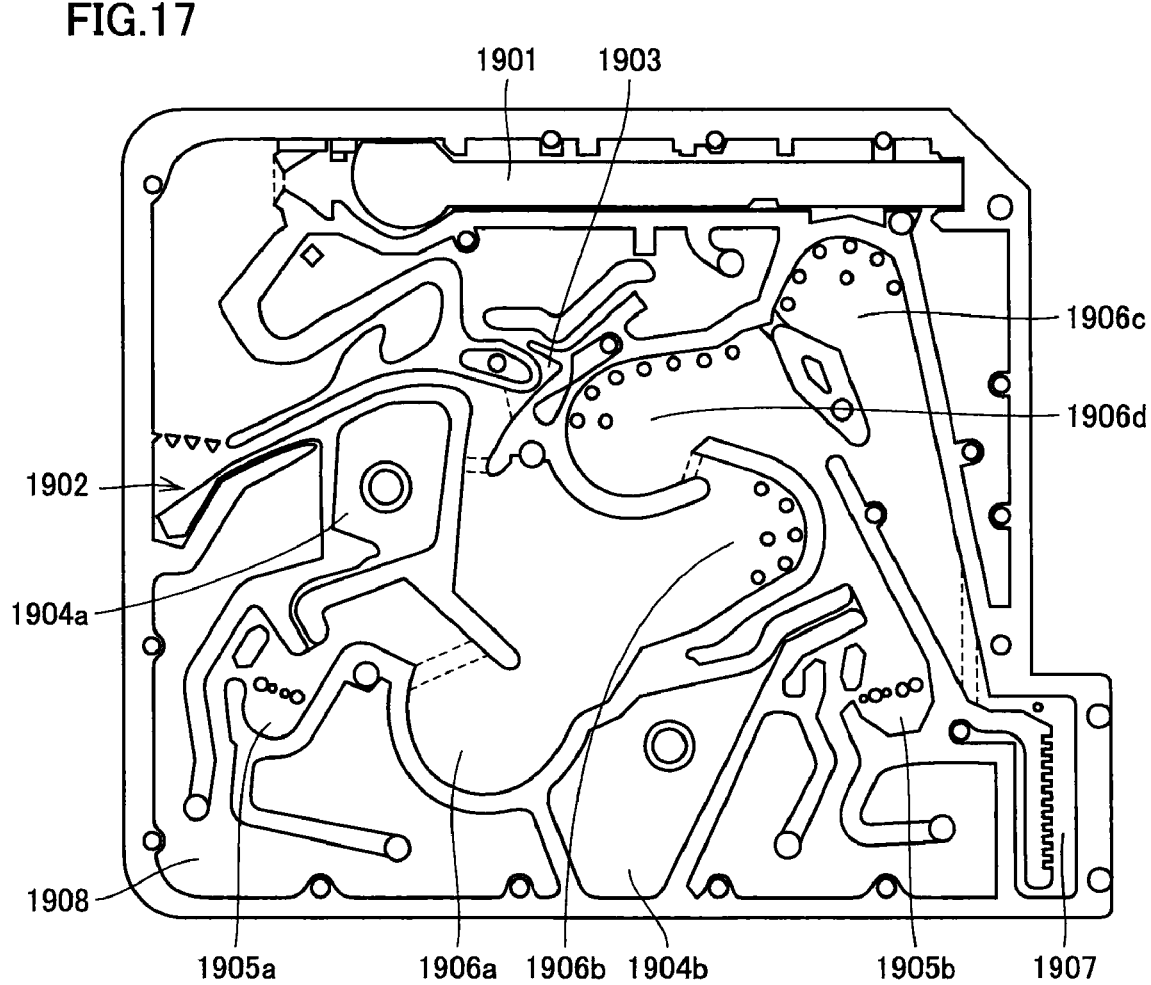
FIG. 17 is a schematic top view of an example of fluid circuits configuration of a microchip for a blood test of the present invention.

Although each of the sites set forth above may be arranged in either the first fluid circuit or the second fluid circuit, it is preferable to gather the sites formed of deep grooves at one of the first and second fluid circuits, and the sites formed of shallow grooves at the other of the first and second fluid circuits. FIG. 15 is a schematic sectional view of a configuration of a mold to form a second substrate having a plurality of shallow grooves at one surface and deep grooves at the other surface. FIG. 16 is a schematic sectional view of a microchip of the present invention produced based on a second substrate 1602, obtained from molds 1501a and 1501b of FIG. 15, a first substrate 1601, and a third substrate 1603. By gathering sites formed of shallow grooves at one of the first and second fluid circuits, a thin and short end mill blade can be employed in cutting out a recess in mold 1501a directed to forming shallow grooves of the second substrate since the cutting depth of the recess may be shallow, as shown in FIG. 15. Accordingly, the width W of rib 1604 constituting shallow grooves can be made smaller (refer to FIG. 16). This is advantageous in that the running out amount of the substrate material is reduced, so that of deviation in the dimension accuracy the fluid circuits and variation in the dimension among microchips can be suppressed. Moreover, by gathering the sites formed of deep grooves at one of the fluid circuits and the sites formed of shallow grooves at the other of the fluid circuits, microfabrication on the mold to be used for producing the second substrate is facilitated. In addition, the fabrication of the mold per se is facilitated. Thus, the productivity of the microchip is improved. Furthermore, since a dead space S that cannot be used for the fluid circuits will not be generated, the scale of integration and density of fluid circuits can be increased, as shown in FIG. 17. In the microchip of FIG. 16, the grooves constituting the first fluid circuit are deeper than the grooves constituting the second fluid circuit.

Among the sites set forth above, the specimen quantification unit and liquid reagent quantification unit are preferably gathered at the second fluid circuit formed of shallow grooves since they do not necessarily require a large volume while dimension accuracy of a more critical level is required. In contrast, the liquid reagent receptacle unit is a site that requires a large volume, and is preferably gathered at the first fluid circuit, differing from the fluid circuits where the specimen quantification unit and liquid reagent quantification unit are disposed.

In the case where the microchip of the present invention includes a liquid reagent receptacle unit, a liquid reagent inlet that is through holes penetrating to the internal liquid reagent receptacle unit is generally formed at the microchip surface (typically, the first substrate surface). Such a microchip generally has a liquid reagent introduced through the liquid reagent inlet, and then a label or seal is attached to the surface of the microchip to close the opening for actual use.

A microchip has various treatments carried out on the fluid such as extraction of a certain component from the specimen (separation of unnecessary component), quantification of a specimen and/or liquid reagent, mixture of the specimen and liquid reagent, introduction of the obtained mixture into the optical measurement cuvette (detection unit) and the like by the sequential application of centrifugal force in an appropriate direction towards the microchip. Application of centrifugal force towards a microchip can be implemented with the microchip mounted on an apparatus (a centrifuge) that can apply centrifugal force. A centrifuge includes, for example, a rotatable stage on which a microchip is placed. Centrifugal force is applied by the rotation of the stage. The mixture eventually obtained by mixing the specimen and liquid reagent is subjected to optical measurement, for example, based on the method of directing light to a site where the mixture is stored (typically, an optical measurement cuvette (detection unit)) and detecting the intensity of the transmitting light (transmissivity) for examination and analysis.

The optical measurement cuvette can be configured as, though not particularly limited to, a columnar cavity having a circular or rectangular cross section extending in, for example, the thickness direction of the microchip. An optical measurement cuvette formed of a cavity is connected to one or both of first and second fluid circuits.

Since the present invention has two layers of fluid circuits, there can be provided a microchip that allows increase in the scale of integration and density of fluid circuits, and that allows examination and analysis of multiple items despite the relatively small area.

Each liquid reagent receptacle unit is connected with a liquid reagent quantification unit via through holes penetrating second substrate 102. For example, liquid reagent receptacle unit 301a (refer to FIG. 3) and liquid reagent quantification unit 411a at section 1 are connected via a through hole 21b. The same applies to other liquid reagent receptacle units and liquid reagent quantification units. By providing two layers of fluid circuits communicating with each other via through holes, the fluid circuits can be used effectively by the shift between the first and second fluid circuits, despite the relatively small area for a microchip. Control of intricate liquid shifting and the like are also allowed.

In microchip 100 of the present embodiment, the grooves provided at second substrate 102 facing first substrate 101 (the grooves constituting the first fluid circuit) is basically made deeper than the grooves provided at the surface of second substrate 102 facing third substrate 103 (grooves constituting the second fluid circuit). Namely, a site and channel where a greater depth is required is provided at the first fluid circuit whereas a site or channel where dimension accuracy of a critical level is more important than the requirement of depth is provided at the second fluid circuit. Accordingly, mixture of deep grooves and shallow grooves in one side fluid circuits can be avoided, allowing a smaller rib width in the formation of a substrate using a mold. Therefore, leakage of resin at the time of substrate welding can be prevented, leading to improvement in the dimension accuracy of the fluid circuits as well as eliminating dimension variation among microchips. By avoiding the mixture of deep grooves and shallow grooves within one side fluid circuits, microfabrication on the mold can be carried out relatively easily, leading to improvement in the mass production of microchips.

The site formed of relatively shallow grooves, accommodating the requirement of preventing/suppressing variation in dimension accuracy and dimension variation among products, are gathered at the second fluid circuit. Thus, as compared to the case where both deep grooves and shallow grooves are provided within one side fluid circuits, microfabrication on the mold can be carried out easily. Fabrication of fluid circuits satisfying the required dimension accuracy is facilitated.

In the present embodiment, liquid reagent receptacle units that require a relatively large capacity (relatively large depth) are gathered at the first fluid circuit, whereas a specimen quantification unit and liquid reagent quantification unit with the requirement of preventing/suppressing variation in dimension accuracy and dimension variation among products are gathered at the second fluid circuit. By improving the dimension accuracy in the specimen quantification unit and liquid reagent quantification unit and preventing/suppressing dimension variation among products, the quantification accuracy is improved and variation in the quantification can be suppressed. Therefore, the performance and reliability of the microchip can be improved. This gathering based on a configuration accommodating the requirements of such sites and channels provides equalization of the depth in each fluid circuits. Accordingly, the occupying ratio of the fluid circuits to the microchip can be increased, allowing a high scale of integration and density of the fluid circuits.

Although a microchip of the present invention and a method of using the microchip have been described based on a microchip having two layers of fluid circuits, the microchip of the present invention may be based having fluid circuits of one layer. Namely, the microchip may be formed by uniting together a first substrate that is a transparent substrate and a second substrate having grooves and/or through holes constituting fluid circuits formed at one side. The microchip of the present invention does not necessarily have to be a multi-test chip, and may be a single test chip that carries out only one type of examination and analysis. Although the present invention requires only at least one of an overflow specimen storage unit and overflow reagent storage unit, preferably both are provided for the purpose of further improving the reliability of the microchip. The number of the overflow specimen storage units and overflow reagent storage units are not particularly limited, and at least one of either the overflow specimen storage unit or overflow reagent storage unit is to be provided. However, a storage unit for storing each liquid reagent and specimen is preferably provided in order to further improve the reliability of the microchip.

In a microchip including two layers of the fluid circuits, the third substrate does not necessarily have to be a transparent substrate. However, at least the surface region constituting the detection unit is preferably transparent to allow measurement of the transmitting light corresponding to the incident light. In the case where the uniting welding method of directing light to the uniting faces of substrates for fusion is to be employed as the method of uniting the first, second and third substrates, the second substrate is preferably an opaque substrate (preferably, a black substrate) and the third substrate is preferably a transparent substrate such that the incident light can be absorbed more efficiently. This facilitates the uniting of the second and third substrates by directing light from the third substrate side to fuse the uniting face of the second substrate. The same applies to the uniting of the first and second substrates.

Although the microchip of the present invention has been described based on a preferable example, the microchip of the present invention is not limited to the embodiment set forth above. For example, the microchip of the present invention does not necessarily have to be a multi-test chip, and may be a single test chip that carries out only one type of examination and analysis. Furthermore, all the sites set forth above do not necessarily have to be included in the present invention. Moreover, one or more of the type of the sites set forth above may be absent. In addition, another site not set forth above may be provided. Further, the number of sites in the microchip is not particularly limited.

Figure 13:
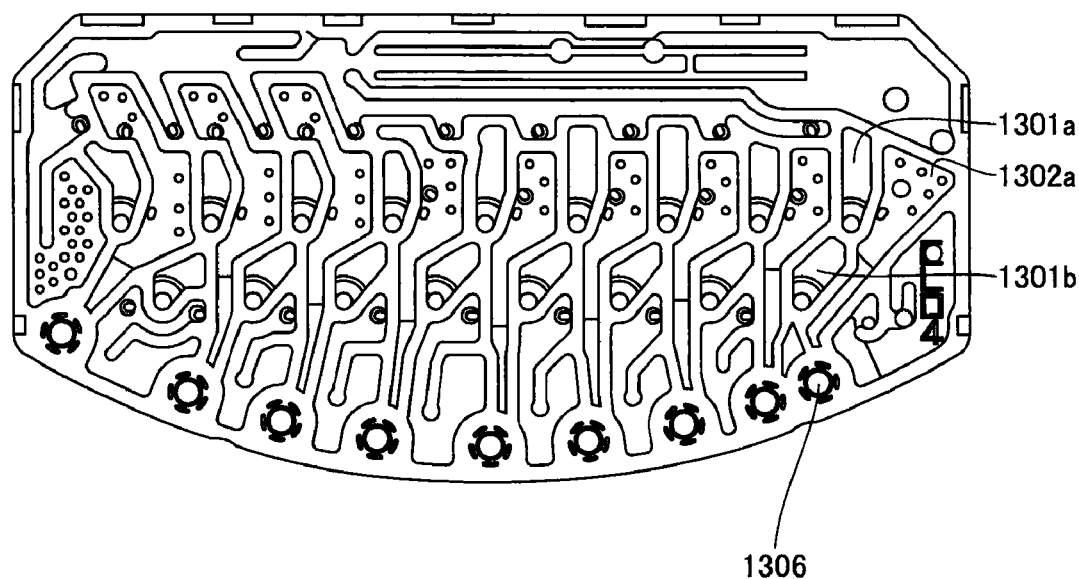
FIGS. 13 and 14 are a top view and a bottom view, respectively, of another example of a second substrate of the microchip of the present invention.
Figure 14:
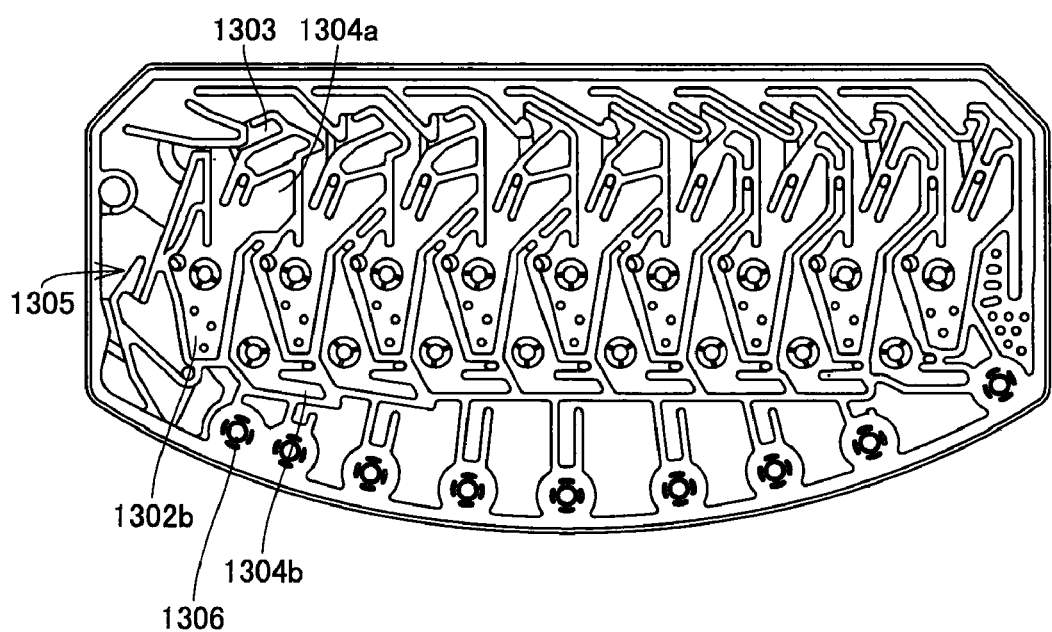

The fluid circuits of the microchip in the present invention (the first fluid circuit and second fluid circuit) is not limited to the configuration of the embodiment set forth above, and may take various configurations. FIGS. 13 and 14 are a top view and a bottom view, respectively, of a second substrate according to another example of a microchip of the present invention. FIG. 13 represents the upper side fluid circuits (first fluid circuit) of the second substrate whereas FIG. 14 represents the lower side fluid circuits (second fluid circuit).

The microchip of FIGS. 13 and 14 is a multi-test chip. Attention is now focused on one section. The first fluid circuit includes liquid reagent receptacle units 1301*a* and 1301*b*, and a mixing unit 1302*a* (refer to FIG. 13). The second fluid circuit includes a specimen quantification unit 1303, liquid reagent quantification units 1304*a* and 1304*b*, a hematocyte separation unit 1305, and a mixing unit 1302*b*. This microchip also includes an optical measurement cuvette (detection unit) 1306. As shown in FIGS. 13 and 14, the microchip of the present invention may have a configuration and shape of fluid circuits differing from that described above.

In the present invention, the third substrate does not necessarily have to be a transparent substrate. However, at least the surface region constituting the detection unit is preferably transparent to allow measurement of the transmitting light corresponding to the incident light. In the case where the uniting welding method of directing light to the uniting faces of substrates for fusion is to be employed as the method of uniting the first, second and third substrates, the second substrate is preferably an opaque substrate (preferably, a black substrate) and the third substrate is preferably a transparent substrate such that the incident light can be absorbed more efficiently. This facilitates the uniting of the second and third substrates by directing light from the third substrate side to fuse the uniting face of the second substrate. The same applies to the uniting of the first and second substrates.

Second Embodiment

The present invention relates to a microchip for a blood test, including a site for separating a component such as lipid that is insoluble to the blood plasma component included in the whole blood sample. The size of the microchip of the present invention is, though not particularly limited to, several centimeters in the horizontal and vertical length, and several millimeters in thickness. The microchip is typically mounted on a device that can apply centrifugal force thereto for use. By applying centrifugal force in an appropriate direction to the microchip, the blood plasma component having lipid and the like removed from the whole blood sample is extracted, followed by quantification, mixture, and the like of the blood plasma component and liquid reagent to detect a certain component in the mixture at the detection unit.

The microchip for a blood test of the present invention has a fluid circuit structure therein. The fluid circuits include, though not particularly limited to, a blood plasma separation unit removing hematocytes from the whole blood sample and also removing suspensions such as lipids to obtain a blood plasma component, a liquid reagent receptacle unit to store a liquid reagent, quantification units to quantify each of a liquid reagent and extracted blood plasma component, a mixing unit to mix the quantified liquid reagent and blood plasma component, and a detection unit to analyze and/or examine the obtained mixture. Other sites are provided, as necessary. There may be two or more sites in one microchip.

Each of the sites constituting fluid circuits are disposed at appropriate positions and connected through minute channels (hereinafter, also simply referred to as "channel") to sequentially allow quantification of the blood plasma component and liquid reagent, mixing of the blood plasma component and liquid reagent, introduction of the mixture to the detection unit, or the like, based on externally applied centrifugal force. Examination and analysis of the mixture at the detection unit (for example, detection of a certain component in the mixture) is carried out generally by, but not particularly limited to, optical measurement such as measuring the absorption spectrum for a mixture stored in a detection unit, including the steps of directing light to the detection unit and identifying the intensity of the output light.

FIG. 17 is a schematic top view of an example of fluid circuits configuration of a microchip for a blood test of the present invention. The microchip of FIG. 17 includes a sample tube mount unit 1901 for fitting in a sample tube such as a capillary in which whole blood is collected, a blood plasma separation unit 1902 removing hematocytes and also suspensions such as lipids from the whole blood extracted from the sample tube to obtain blood plasma component, a first quantification unit 1903 to quantify the separated blood plasma component, two liquid reagent receptacle units 1904*a* and 1904*b* to store a liquid reagent, a second quantification unit 1905*a* to quantify a liquid reagent, a third quantification unit 1905*b*, mixing units 1906*a*-1906*d* to mix the blood plasma component and liquid reagent, and a detection unit 1907 for carrying out examination and/or analysis on the obtained mixture. The number of liquid reagent receptacle units and mixing units is not limited to those shown in FIG. 17. In the microchip of the present invention, the blood plasma separation unit includes a suspension removal unit to remove suspensions such as lipids.

Figure 18:
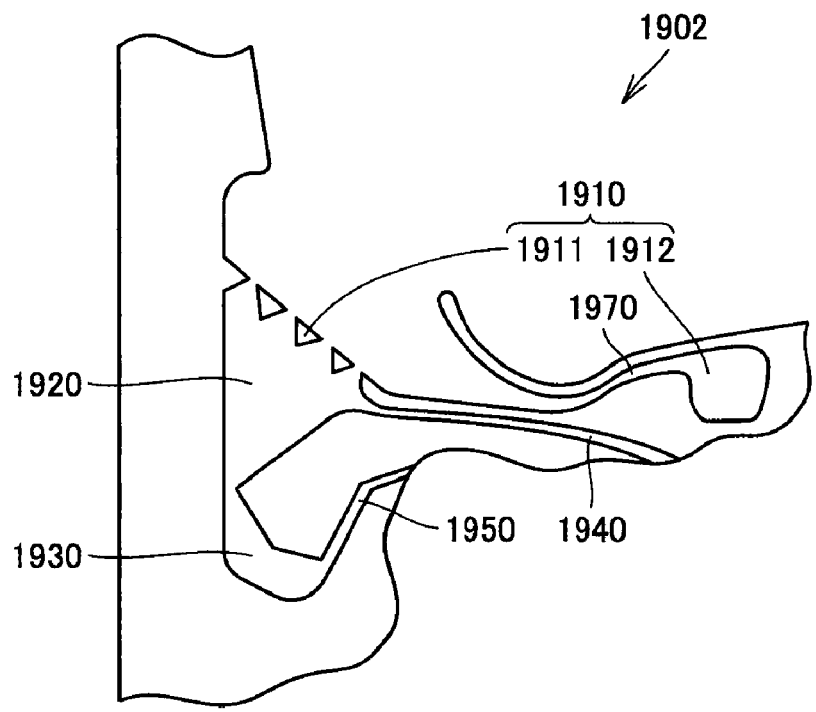
FIG. 18 is a schematic enlarged top view of a blood plasma separation unit in the microchip of FIG. 17.

FIG. 18 is a schematic enlarged top view of blood plasma separation unit 1902 in the microchip of FIG. 17. Referring to FIG. 18, blood plasma separation unit 1902 includes a suspension removal unit 1910 formed of a plurality of columnar structures 1911 arranged in a row in a discrete manner and a suspension storage unit 1912 to store the removed suspensions such as lipids, a blood plasma reservoir 1920 to store mainly the separated blood plasma component, and a hematocyte reservoir 1930 communicating with blood plasma reservoir 1920 to store mainly the separated hematocytes. A first channel 1940 to introduce the separated blood plasma component to first quantification unit 1903 is connected with blood plasma reservoir 1920. The other end of hematocyte reservoir 1930 is connected to a second channel 1950 to introduce the separated component mainly constituted of hematocytes to the waste reservoir unit (waste reservoir 1908 in FIG. 17) that stores the same as waste.

The inclusion of suspension removal unit 1910 in blood plasma separation unit 1902 allows suspensions such as lipids floating in proximity to the surface of the blood plasma component (liquid level) to be removed at blood plasma separation unit 1902 during separation of the whole blood sample introduced into blood plasma separation unit 1902 into the blood plasma component and hematocyte component by application of centrifugal force. Therefore, examination and analysis on the mixture can be carried out at the detection unit without being marred by suspensions, allowing an accurate examination and analysis on the plasma component.

Figure 19:
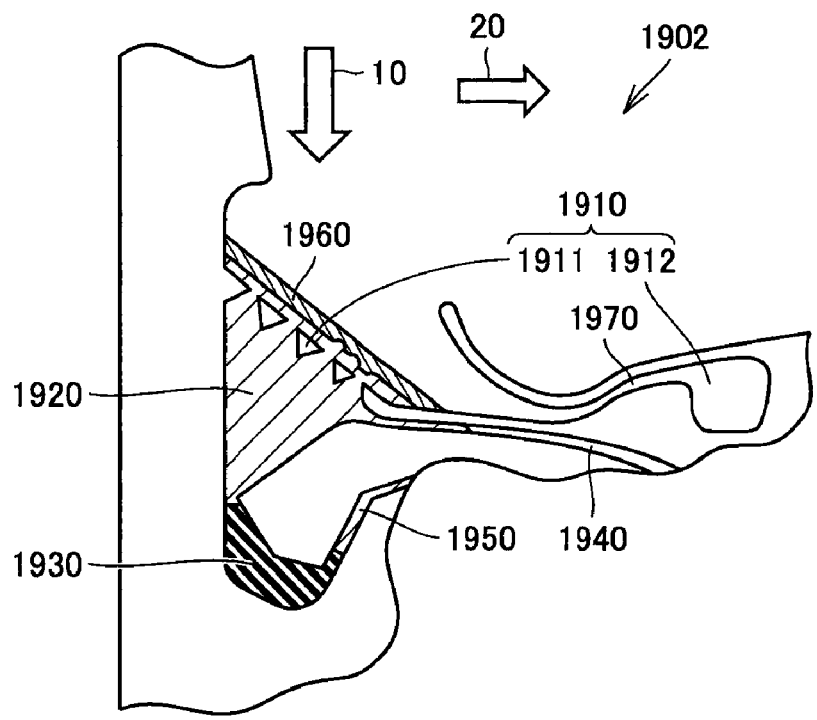
FIG. 19 is a schematic top view representing the separated state of the blood plasma component and hematocyte component in the whole blood sample as a result of introduction of the whole blood sample into a blood plasma separation unit 1902 of FIG. 18 and application of centrifugal force.

FIG. 19 is a schematic top view of the separated state of the blood plasma component and hematocyte component from the whole blood sample, after introduction of the whole blood sample into blood plasma separation unit 1902 of FIG. 18 and application of centrifugal force. As shown in FIG. 19, the whole blood sample introduced into the fluid circuits is guided into blood plasma separation unit 1902 by the application of the centrifugal force in the direction of arrow 10 of FIG. 19, further subjected to centrifugation by the application of centrifugal force in the same direction, resulting in the separation of the blood plasma component and hematocyte component. Since the specific gravity of the hematocyte component is larger than the blood plasma component, the hematocyte component is stored in hematocyte reservoir 1930, whereas the blood plasma component is stored mainly in blood plasma reservoir 1920, as the upper layer to the hematocyte component layer. The interface between the plasma component layer and the hematocyte component layer may vary depending upon the content of the hematocyte component in the whole blood sample. In the case where the whole blood sample introduced into blood plasma separation unit 1902 includes suspensions such as lipids, the centrifugation on the whole blood sample thereat will result in suspensions 1960 separated by the application of the centrifugal force to be located in proximity to the surface of the blood plasma component layer (interface). As used herein, "suspension" is the substance having a lower specific gravity than the blood plasma component, insoluble or not readily soluble with respect to the plasma component, such as lipid.

The microchip of the present invention is configured such that the surface of the separated blood plasma component layer at the side where suspensions are present (interface) is located upper than the line corresponding to the alignment of columnar structures 1911 (in other words, such that the blood plasma component will overflow from the alignment line of columnar structures 1911), by appropriately setting the capacity of blood plasma reservoir 1920 and hematocyte reservoir 1930, and the location of the plurality of columnar structures 1911 in one row. Accordingly, suspensions 1960 present in proximity to the surface of the blood plasma component layer separated by the application of centrifugal force in the direction of arrow 10 in FIG. 19 will be located upper than the line corresponding to the alignment of one row of columnar structures 1911.

The separated suspensions 1960 then move to suspension storage unit 1912 to be stored therein as a result of application of centrifugal force in the direction of arrow 20 in FIG. 19. By the centrifugal force in the direction of arrow 20, the blood plasma component having the hematocyte component and suspensions 1960 removed are introduced into first quantification unit 1903 (not shown in FIG. 19) via first channel 1940, and the separated hematocyte component located in hematocyte reservoir 1930 is introduced into waste reservoir 1908 (not shown in FIG. 19) via second channel 1950.

Figure 20:
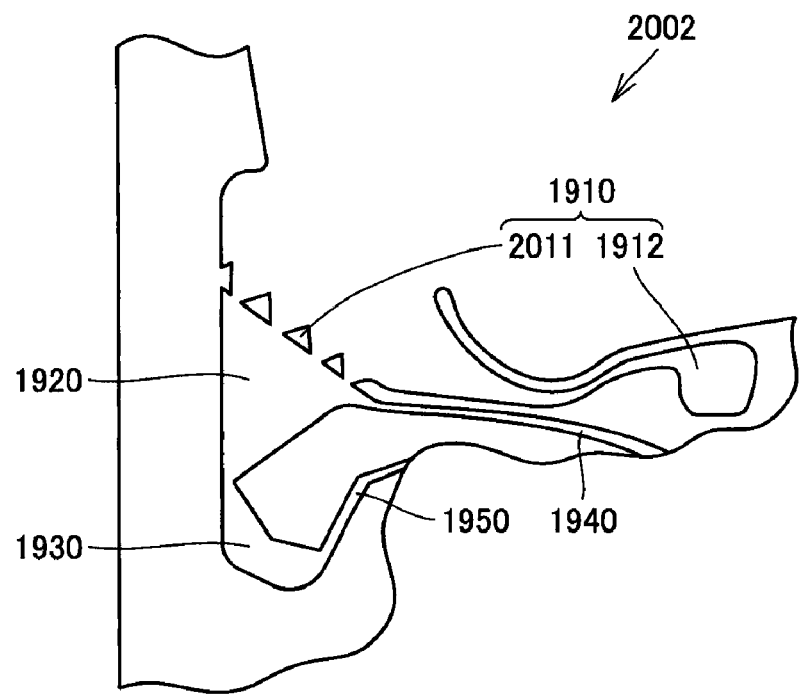
FIGS. 20, 21, and 22 are schematic enlarged top views of examples of a blood plasma separation unit of the present invention.

The number of columnar structures 1911 is, though not particularly limited to, one or more. As shown in FIG. 18, in the case where a plurality of columnar structures are disposed apart from each other, the width of the gap therebetween can be set to 50 to 500 μm, for example. The cross section of columnar structure 1911 is not particularly limited, and may be a polygonal cross section such as a triangle or rectangle, or a circular or optical cross section. The diameter of the cross section of columnar structure 1911 can be set to 50 to 500 μm, for example. The orientation of the cross section of columnar structure 1911, when taking a triangular shape, is not particularly limited. For example, columnar structure 1911 may be oriented such that the width of the opening formed between columnar structures becomes wider in the downward direction, as shown in FIG. 18, or such that the width of the opening becomes wider in the upward direction, as shown in blood plasma separation unit 2002 of FIG. 20. The former is advantageous in that the flow of the separated suspensions 1960 into first quantification unit 1903 through the gaps of columnar structures 1911 can be prevented more effectively during the passage of the blood plasma component to first quantification unit 1903 by application of centrifugal force. The latter is advantageous in that the flow of the blood plasma component located lower than the line corresponding to one row of columnar structures 2011 into suspension storage unit 1912 through the gaps of columnar structures 2011 can be prevented more effectively.

Figure 21:
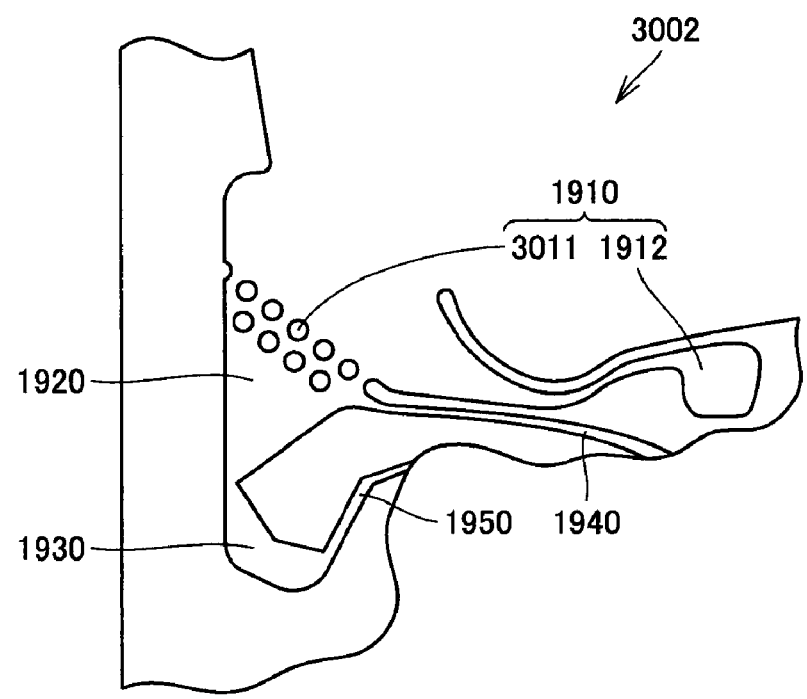

Further, as shown in blood plasma separation unit 3002 of FIG. 21, a plurality of discrete columnar structures 3011 may be arranged to form a plurality of rows. Accordingly, the passage of the separated suspensions to the first quantification unit and/or the passage of the blood plasma component located lower than columnar structures 3011 towards suspension storage unit 1912 can be prevented more effectively. The cross section of the columnar structure is not particularly limited in this case.

The suspension storage unit will be described hereinafter. The suspension storage unit of the present invention is arranged upper than the line corresponding to the columnar structures, i.e. at the surface side where the suspensions of the blood plasma component are present based on the line of the columnar structures as the reference, so as to store suspensions present in proximity to the surface of the blood plasma component. Referring to FIG. 18, suspension storage unit 1912 is preferably connected to a region located upper than the line of columnar structures at blood plasma reservoir 1920.

First channel 1940 is a path for introduction of the blood plasma component having suspensions 1960 and the hematocyte component removed to first quantification unit 1903. First channel 1940 is connected to a region located lower than the line constituted of columnar structures at blood plasma reservoir 1920.

Figure 22:
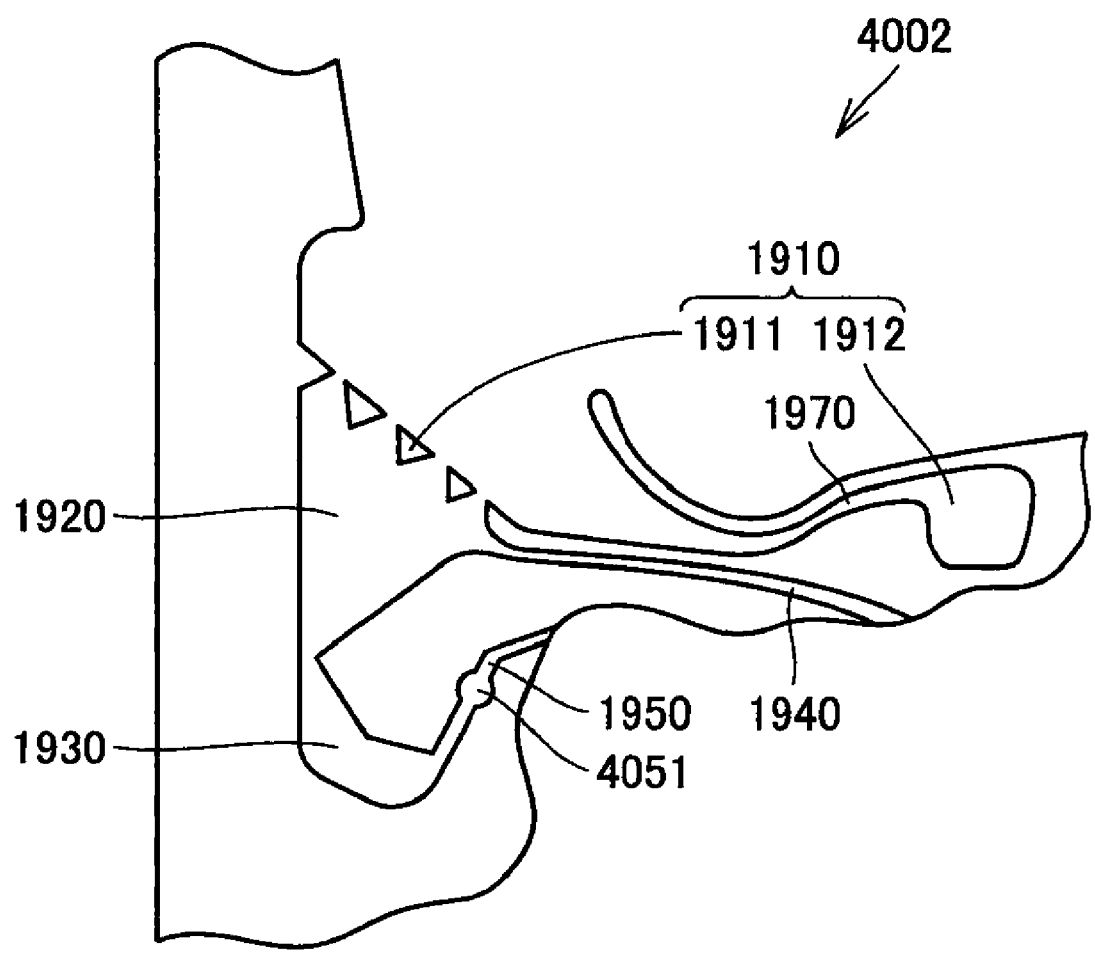
Figure 23:
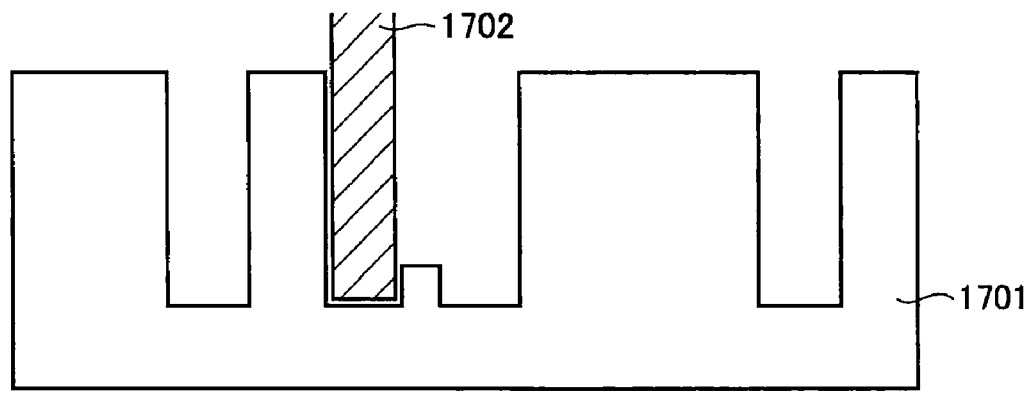
FIG. 23 is a schematic sectional view of a configuration of a mold used to form a substrate having grooves constituting fluid circuits, employed in a conventional microchip.
Figure 24:
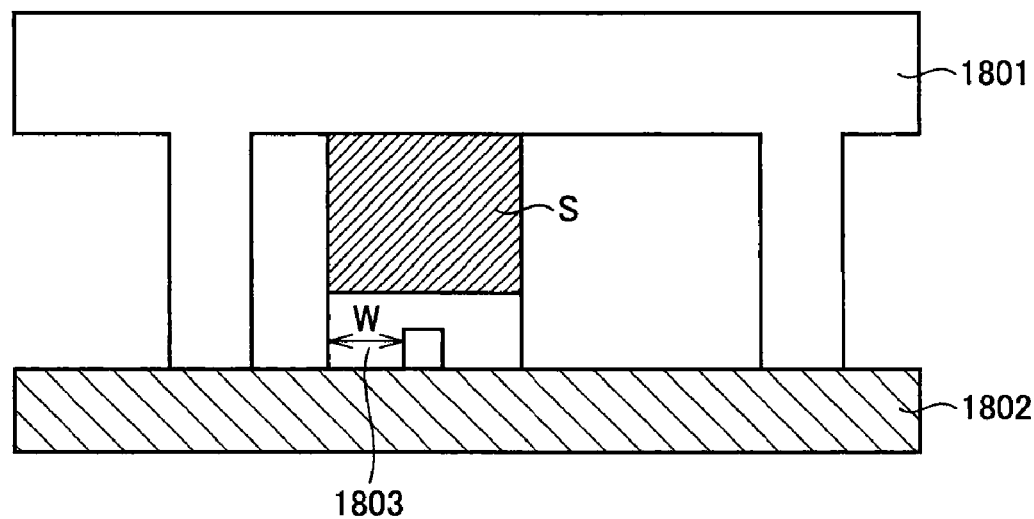
FIG. 24 is a schematic sectional view of a microchip produced using the substrate obtained from the mold of FIG. 23.

Second channel 1950 is a path for introduction of the separated hematocyte component to the waste reservoir (waste reservoir 1908 in FIG. 17). The separated hematocyte component in the hematocyte reservoir 1930 flows into waste reservoir 1908 by the application of centrifugal force in the direction of arrow 20 in FIG. 19. As shown in blood plasma separation unit 4002 of FIG. 22, hematocyte detection unit 4051 to identify the ratio of the hematocyte to the whole cell may be provided at second channel 1950. The configuration of hematocyte detection unit 4051 has, though not particularly limited to, a circular or tubular cross section. The depth direction of the tube corresponds to the thickness direction of the microchip. The amount of the hematocyte component in the whole blood can be identified, taking advantage of the fact that the transmissivity of light directed to hematocyte detection unit 4051 differs depending upon the liquid (blood plasma component or hematocyte component) in hematocyte detection unit 4051. The direction of the radiation light may be parallel with the thickness direction of the microchip, or parallel with the surface of the microchip, though not particularly limited.

An example of an operating method of the microchip of FIG. 17 will be described hereinafter. The operation method that will be described hereinafter is only a way of example, and not of limitation. First, a sample tube in which whole blood sample is collected is fitted in sample tube mount unit 1901. Centrifugal force is applied to the microchip in the leftward direction in FIG. 17 (hereinafter, simply referred to as leftward; the same applies to other directions). The whole blood sample in the sample tube is taken out, and then introduced to blood plasma separation unit 1902 to be subjected to centrifugation by downward centrifugal force, resulting in the separation into the blood plasma component and hematocyte component. In the case where suspensions such as lipids are included in the whole blood sample, such suspensions will also be separated. Moreover, by the downward centrifugal force, a liquid reagent X in liquid reagent receptacle unit 1904a is quantified at second quantification unit 1905a.

The separated blood plasma component is introduced into first quantification unit 1903 by the rightward centrifugal force. At this stage, the separated suspensions move to the suspension storage unit whereas the separated hematocyte component moves to waste reservoir 1908. Liquid reagent X subjected to quantification moves to mixing unit 1906b and a liquid reagent Y in liquid reagent receptacle unit 1904b is output therefrom.

In response to the downward centrifugal force, the quantified blood plasma component and liquid reagent X are mixed at mixing unit 1906a, and liquid reagent Y is quantified at third quantification unit 1905b. Then, the centrifugal force is sequentially applied rightward, downward, and rightward to cause the mixture to run between mixing units 1906a and 1906b to effect sufficient mixing of the mixture. Next, in response to the upward centrifugal force, the mixture of liquid reagent X and the blood plasma component as well as quantified liquid reagent Y are mixed at mixing unit 1906c. The centrifugal force is sequentially applied leftward, upward, leftward and upward to cause the mixture to run between mixing units 1906c and 1906d to effect sufficient mixing of the mixture.

Lastly, by the rightward centrifugal force, the mixture in mixing unit 1906c is introduced into detection unit 1907 to be subjected to examination and analysis based on the optical scheme. This examination and analysis can be carried out accurately since suspensions such as lipids are removed at blood plasma separation unit 1902.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip including fluid circuits therein, the microchip comprising a first transparent substrate and a second substrate joined to the first transparent substrate, said second substrate having grooves provided at a substrate surface and said fluid circuits being defined by a substrate surface of said first transparent substrate facing said second substrate and said grooves, wherein said fluid circuits comprise:
a first liquid reagent receptacle unit to store a first liquid reagent,
a first liquid reagent quantification unit connected to said first liquid reagent receptacle unit, wherein the first liquid reagent quantification unit quantifies said first liquid reagent,
a first overflow reagent storage unit connected to said first liquid reagent quantification unit, wherein the first overflow reagent storage unit stores said first liquid reagent overflowing from said first liquid reagent quantification unit and has a site irradiated with light to detect absence or presence of said first liquid reagent,
a specimen quantification unit that guantifies a specimen, said specimen quantification unit being a distinct unit from said first liquid regent quantification unit,
an overflow specimen storage unit connected to said specimen quantification unit, wherein the overflow specimen storage unit stores said specimen overflowing from said specimen quantification unit and has a site irradiated with light to detect absence or presence of said specimen, and
a first mixing unit connected to said first liquid reagent quantification unit and said specimen quantification unit, wherein the first mixing unit generates a first mixture by mixing a quantified specimen with a quantified first liquid reagent, said first mixing unit being a distinct unit from said first liquid reagent quantification unit and said specimen quantification unit.

2. The microchip according to claim 1, further comprising:
a second liquid reagent receptacle unit arranged to store a second liquid reagent,
a second liquid reagent quantification unit connected to said second liquid reagent receptacle unit and arranged to quantify said second liquid reagent,
a second mixing unit connected to said first mixing unit and arranged to generate a second mixture by mixing said first mixture with said second liquid reagent, and
a detection unit connected to said second mixing unit and arranged to analyze said second mixture by optical measurement.

3. The microchip according to claim 1, wherein said first transparent substrate has a through hole and has a specimen inlet which is connected to said specimen quantification unit via said through hole.

4. The microchip according to claim 1, including a plurality of overflow liquid storage units, wherein said plurality of overflow liquid storage units are disposed on a circumference of the same circle at a surface of said second substrate.

5. The microchip according to claim 1, including two layers of fluid circuits therein, formed by uniting together a first substrate that is a transparent substrate, a second substrate having groves provided at both surfaces of the substrate and through holes penetrating in the thickness direction, and a third substrate.

6. The microchip according to claim 5, including a plurality of overflow liquid storage units, wherein one of said two layers of fluid circuits, located at a side of said first substrate, includes all the overflow liquid storage units.

7. The microchip according to claim 1, wherein said second substrate is an opaque substrate.

8. The microchip according to claim 7, wherein said second substrate is a black substrate.

* * * * *